United States Patent
Miyairi et al.

(10) Patent No.: US 8,346,497 B2
(45) Date of Patent: Jan. 1, 2013

(54) METHOD FOR TESTING SEMICONDUCTOR FILM, SEMICONDUCTOR DEVICE AND MANUFACTURING METHOD THEREOF

(75) Inventors: Hidekazu Miyairi, Tochigi (JP); Hideyuki Ebine, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 10/808,499

(22) Filed: Mar. 25, 2004

(65) Prior Publication Data

US 2004/0254769 A1    Dec. 16, 2004

(30) Foreign Application Priority Data

Mar. 26, 2003 (JP) ................................ 2003-085096

(51) Int. Cl.
*G01N 21/00* (2006.01)
(52) U.S. Cl. .................... 702/117; 702/183; 382/149
(58) Field of Classification Search .............. 702/57–59, 702/75, 76, 108, 117, 127, 182, 183, 185, 702/189; 382/144, 145, 149
See application file for complete search history.

(56) References Cited

U.S. PATENT DOCUMENTS

| | | | |
|---|---|---|---|
| 5,091,963 A * | 2/1992 | Litt et al. ...................... | 382/149 |
| 5,835,614 A * | 11/1998 | Aoyama et al. ................ | 382/104 |
| 5,854,803 A | 12/1998 | Yamazaki et al. | |
| 6,051,834 A * | 4/2000 | Kakibayashi et al. ........ | 250/311 |
| 6,647,148 B2 * | 11/2003 | Ozawa et al. ................ | 382/199 |
| 6,836,532 B2 * | 12/2004 | Durst et al. ...................... | 378/73 |
| 6,861,614 B1 * | 3/2005 | Tanabe et al. ............ | 219/121.66 |
| 6,870,126 B2 | 3/2005 | Jyumonji et al. | |
| 6,933,185 B2 | 8/2005 | Wada et al. | |
| 6,937,753 B1 * | 8/2005 | O'Dell et al. ................. | 382/141 |
| 6,975,386 B2 * | 12/2005 | Tsumura et al. ............... | 356/30 |
| 7,102,750 B2 | 9/2006 | Takami | |
| 7,186,602 B2 | 3/2007 | Jyumonji et al. | |
| 7,345,746 B2 | 3/2008 | Takami | |

(Continued)

FOREIGN PATENT DOCUMENTS

JP    08-195357    7/1996

(Continued)

OTHER PUBLICATIONS

Matsuhashi, S., et al., "A Proposal of the Modified HSV Colour System Suitable for Human Face Extraction," The Journal of the Institute of Television Engineers of Japan, vol. 49, No. 6, Jun. 20, 1995, pp. 787-797.

*Primary Examiner* — Jeffrey R West
(74) *Attorney, Agent, or Firm* — Eric J. Robinson; Robinson Intellectual Property Law Office, P.C.

(57) ABSTRACT

The invention provides a method for testing a semiconductor film, a manufacturing method of a semiconductor film, a laser crystallization method, a laser crystallization device, and a laser crystallization system, for testing a laser crystallized semiconductor film, which require less time, have sufficient reliability, are excellent in cost management and applicable to mass production. In the method for testing a semiconductor film having an improved crystallinity by irradiating an energy light, the tested semiconductor film is photographed in a dark field digital image and then the luminance of the digital image is calculated by a computer in a constant direction for testing.

38 Claims, 24 Drawing Sheets
(1 of 24 Drawing Sheet(s) Filed in Color)

U.S. PATENT DOCUMENTS

| | | | |
|---|---|---|---|
| 2002/0001405 A1* | 1/2002 | Yonezawa | 382/149 |
| 2002/0031249 A1* | 3/2002 | Komuro et al. | 382/149 |
| 2002/0059896 A1* | 5/2002 | Yamaguchi et al. | 117/7 |
| 2003/0016349 A1* | 1/2003 | Tsumura et al. | 356/237.2 |
| 2003/0142298 A1* | 7/2003 | Ujihara et al. | 356/237.2 |
| 2004/0203219 A1* | 10/2004 | Kasahara et al. | 438/487 |
| 2004/0228526 A9* | 11/2004 | Lin et al. | 382/165 |
| 2005/0041226 A1* | 2/2005 | Tanaka et al. | 355/53 |
| 2007/0096103 A1 | 5/2007 | Jyumonji et al. | |

FOREIGN PATENT DOCUMENTS

| | | | |
|---|---|---|---|
| JP | 2000-031229 | | 1/2000 |
| JP | 2000031229 A | * | 1/2000 |
| JP | 2000031229 A | * | 1/2000 |
| JP | 2000-114174 | | 4/2000 |
| JP | 2000114174 A | * | 4/2000 |
| JP | 2000114174 A | * | 4/2000 |
| JP | 2001-196430 | | 7/2001 |
| JP | 2002-176009 A | | 6/2002 |
| JP | 2002-217107 | | 8/2002 |
| JP | 2002217107 A | * | 8/2002 |
| JP | 2002217107 A | * | 8/2002 |
| JP | 2002-305146 A | | 10/2002 |
| JP | 2003-163167 A | | 6/2003 |
| JP | 2004-119617 A | | 4/2004 |
| JP | 2004-146782 A | | 5/2004 |

* cited by examiner

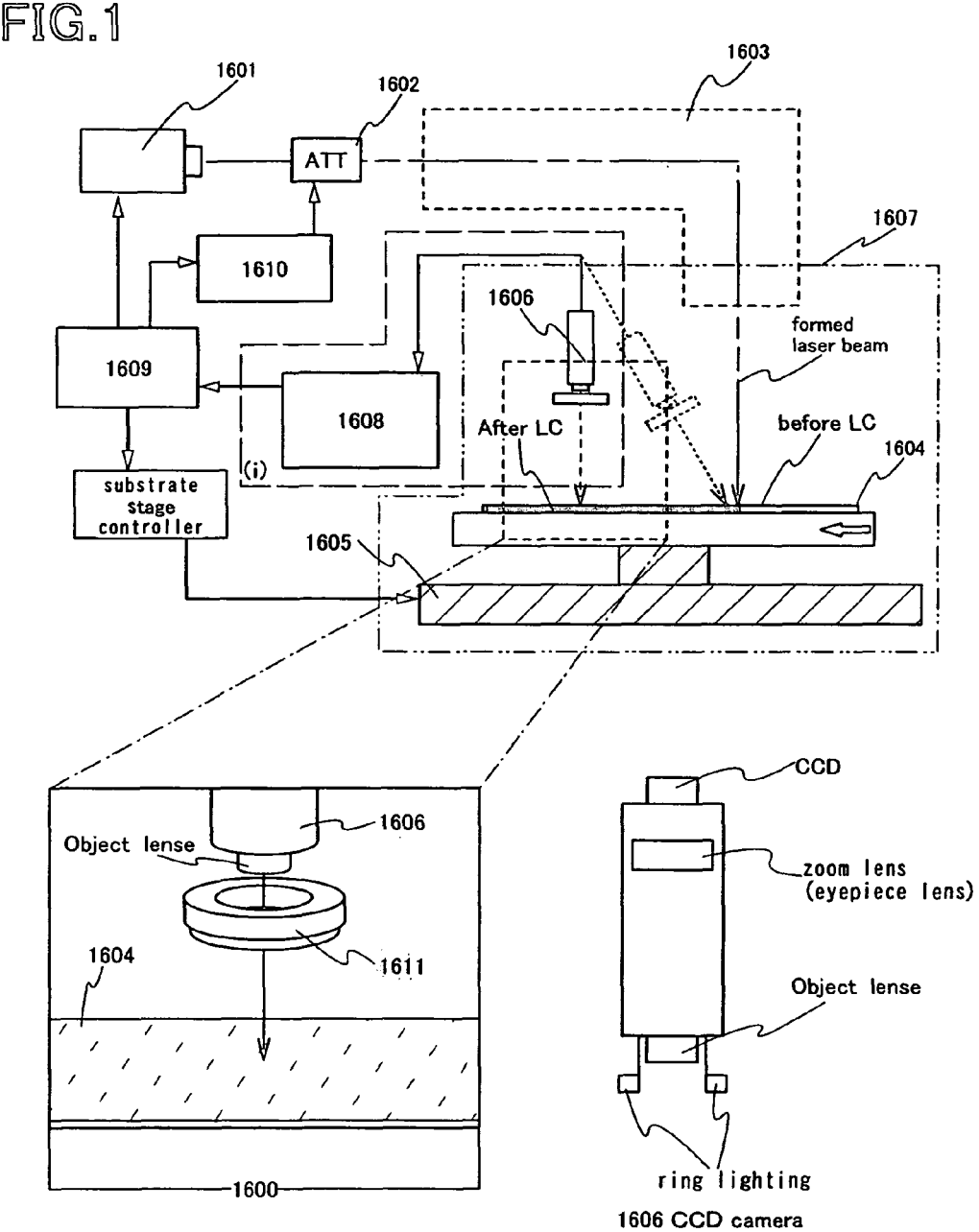

B:luminance value $Bt_{Y_1} = B(X_1,Y_1) + B(X_2,Y_1) + B(X_3,Y_1) + \cdots + B(X_n,Y_1)$ $Bt_{Y_2} = B(X_1,Y_2) + B(X_2,Y_2) + B(X_3,Y_2) + \cdots + B(X_n,Y_2)$ $Bt_{Y_3} = B(X_1,Y_3) + B(X_2,Y_3) + B(X_3,Y_3) + \cdots + B(X_n,Y_3)$ $\vdots \qquad \vdots \qquad \vdots \qquad \vdots \qquad \vdots$ $Bt_{Y_m} = B(X_1,Y_m) + B(X_2,Y_m) + B(X_3,Y_m) + \cdots + B(X_n,Y_m)$

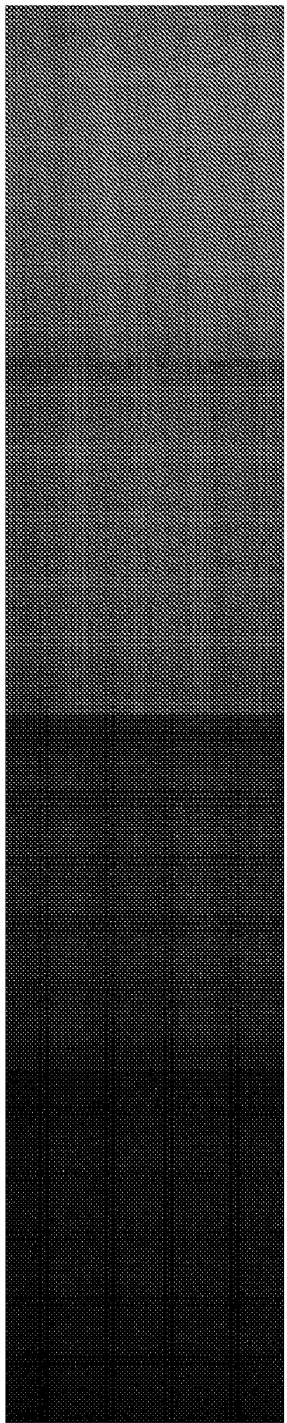
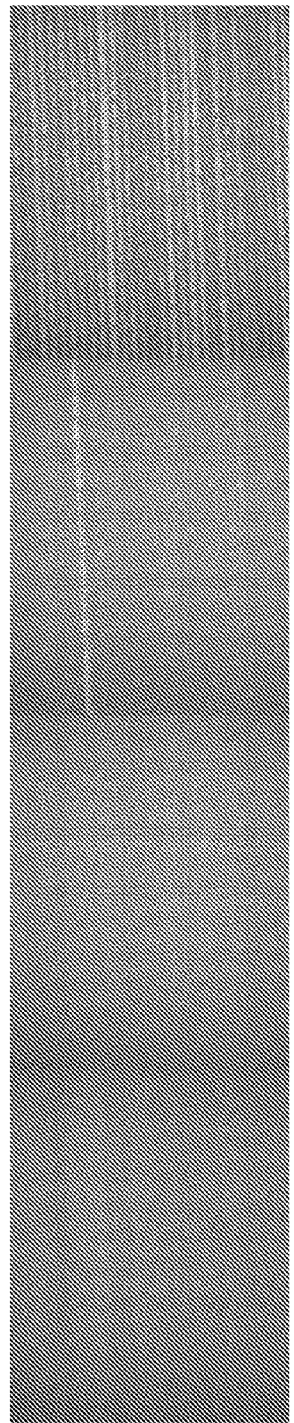
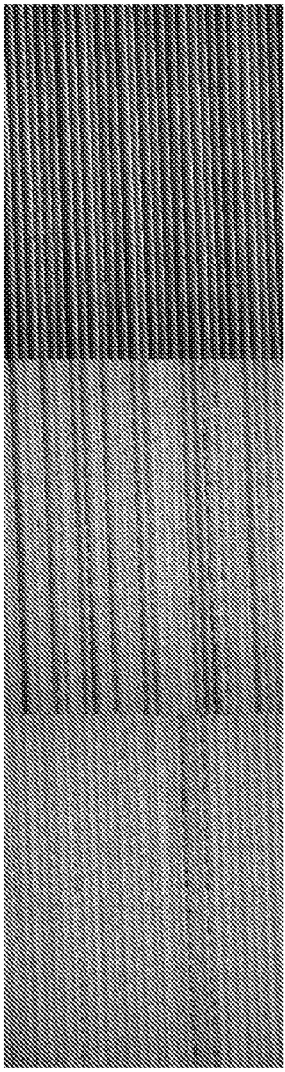
Fig. 7A  379.0mJ/cm²
Fig. 7B  390.3mJ/cm²
Fig. 7C  404.5mJ/cm²
Fig. 7D  411.2mJ/cm²
Fig. 7E  423.9mJ/cm²
Fig. 7F  432.7mJ/cm²
Fig. 7G  443.6mJ/cm²
Fig. 7H  455.7mJ/cm²
Fig. 7I  466.3mJ/cm²
Fig. 7J  475.4mJ/cm²
Fig. 7K  487.2mJ/cm²
After LC, CCD original image (dark field) × 100 (Note that this is reduced 16%.) Under line: optimal condition in functional inspection

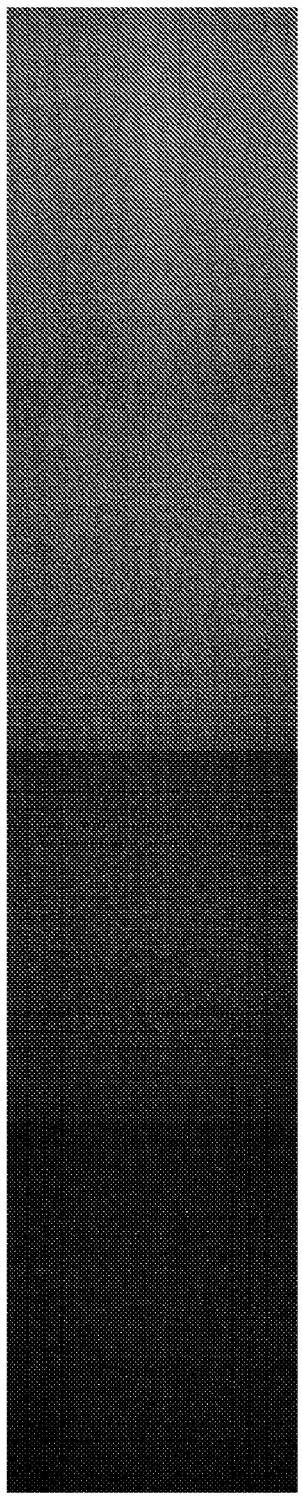
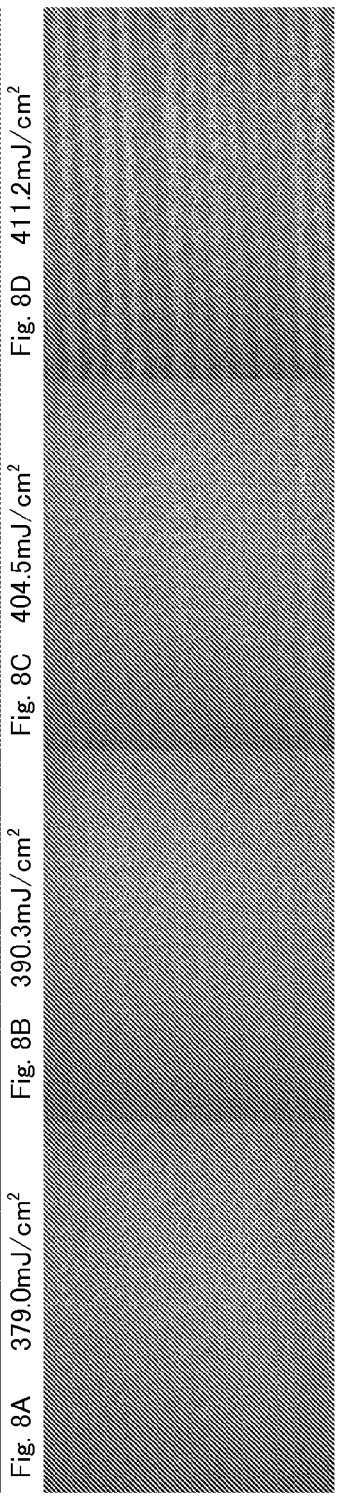
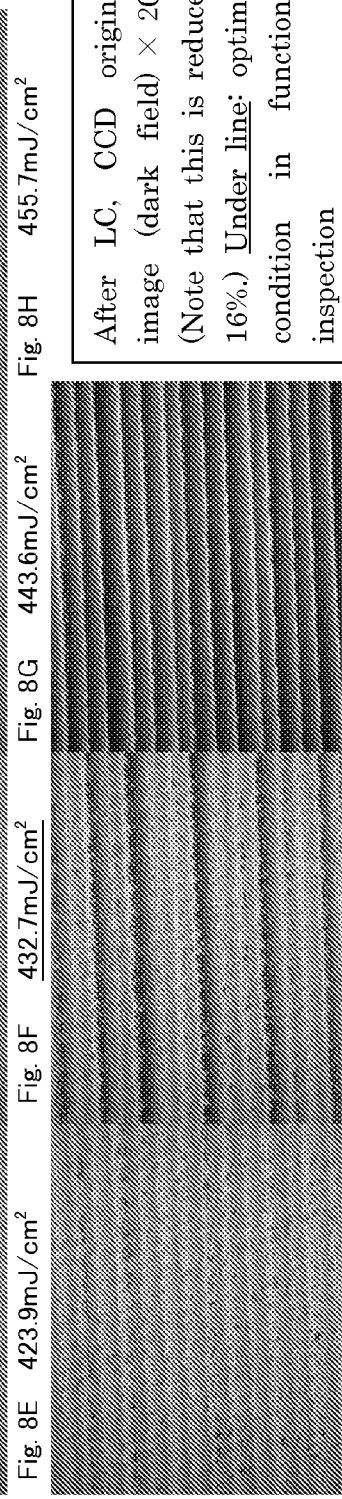
Fig. 8A 379.0mJ/cm² Fig. 8B 390.3mJ/cm² Fig. 8C 404.5mJ/cm² Fig. 8D 411.2mJ/cm²
Fig. 8E 423.9mJ/cm² Fig. 8F 432.7mJ/cm² Fig. 8G 443.6mJ/cm² Fig. 8H 455.7mJ/cm²
Fig. 8I 466.3mJ/cm² Fig. 8J 475.4mJ/cm² Fig. 8K 487.2mJ/cm²
After LC, CCD original image (dark field) × 200 (Note that this is reduced 16%.) Under line: optimal condition in functional inspection

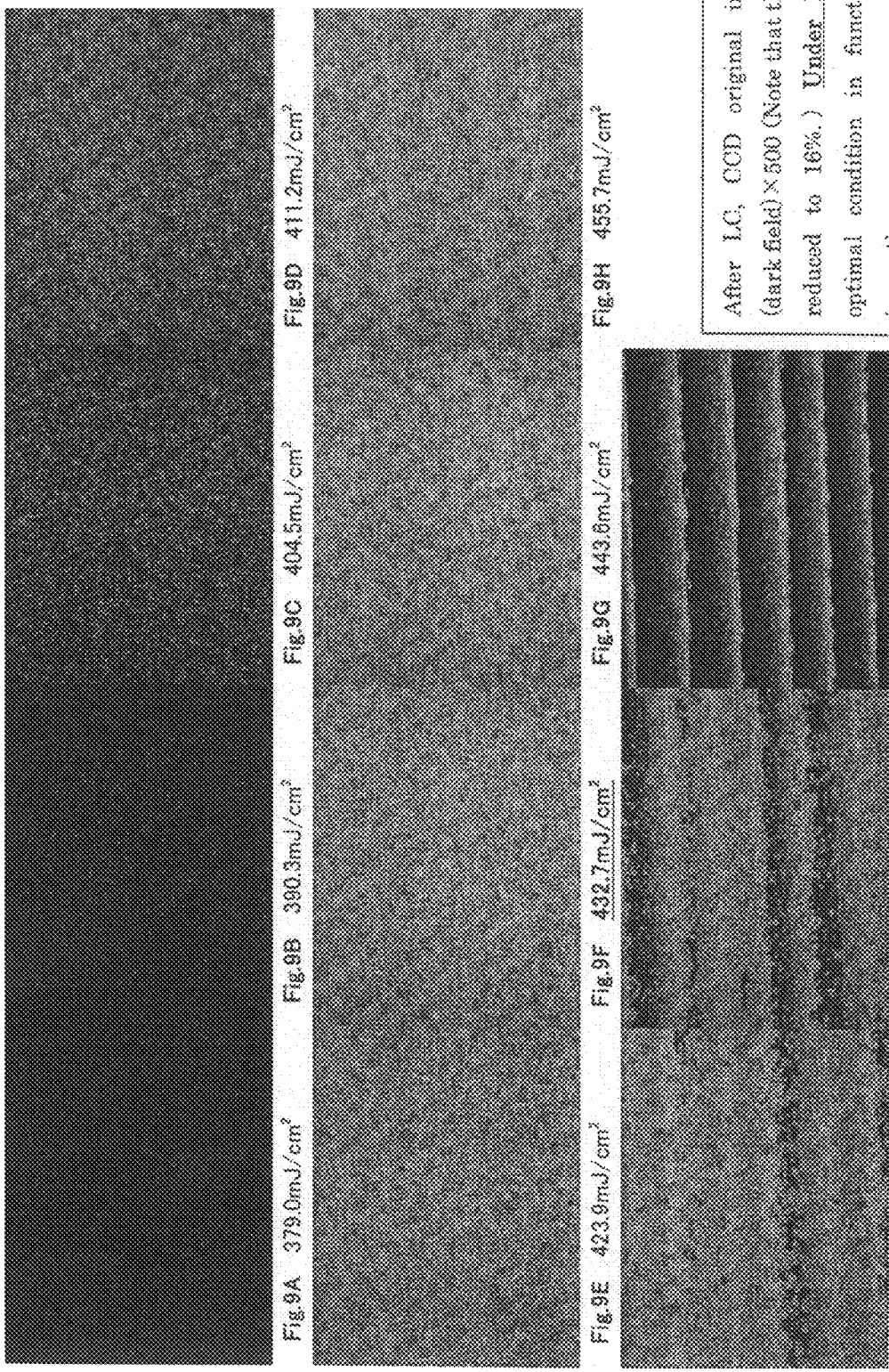

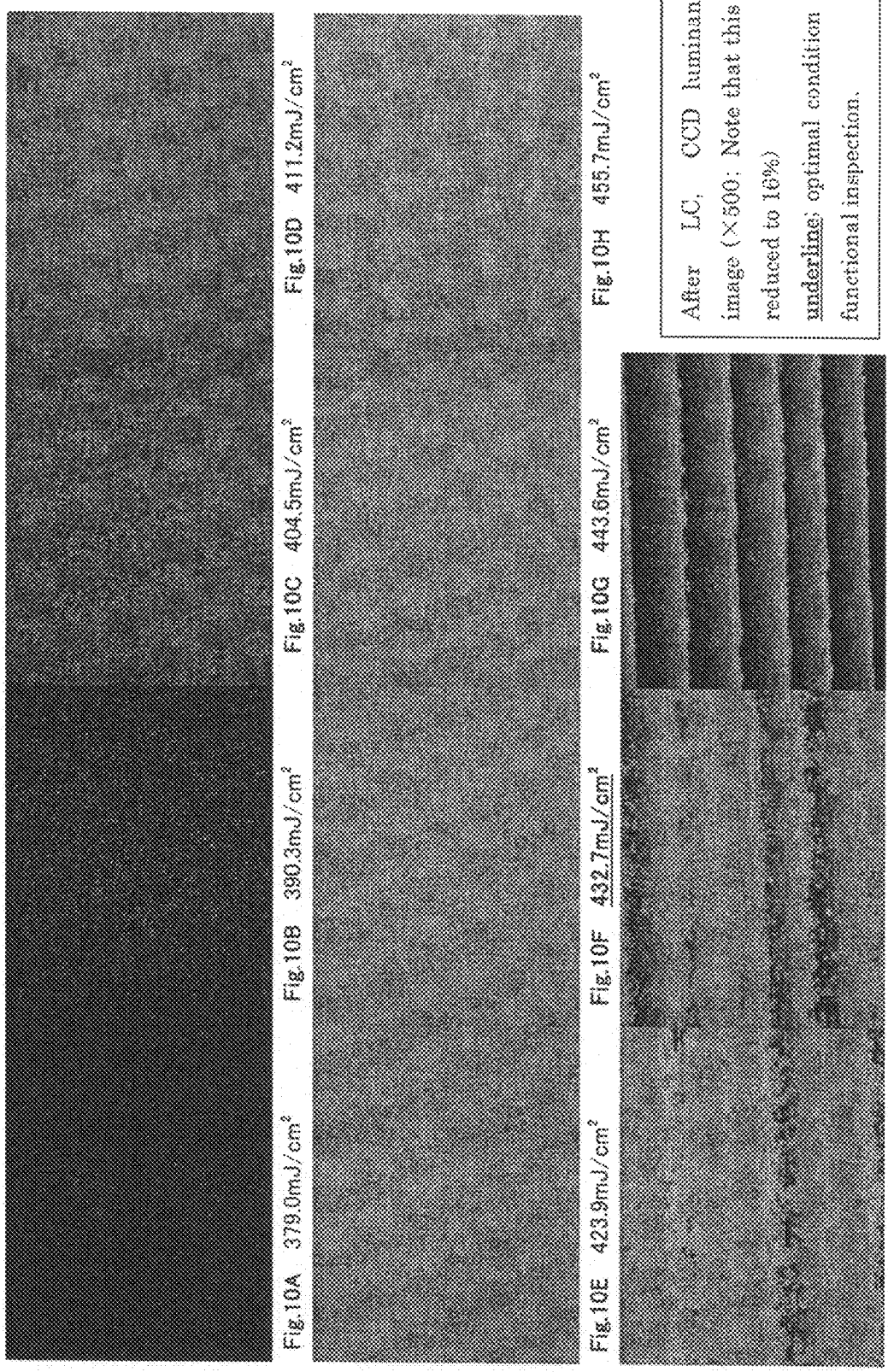

After LC, CCD extra image (×500; Note that this is reduced to 16%) optimal <u>underline</u>: condition in functional inspection.

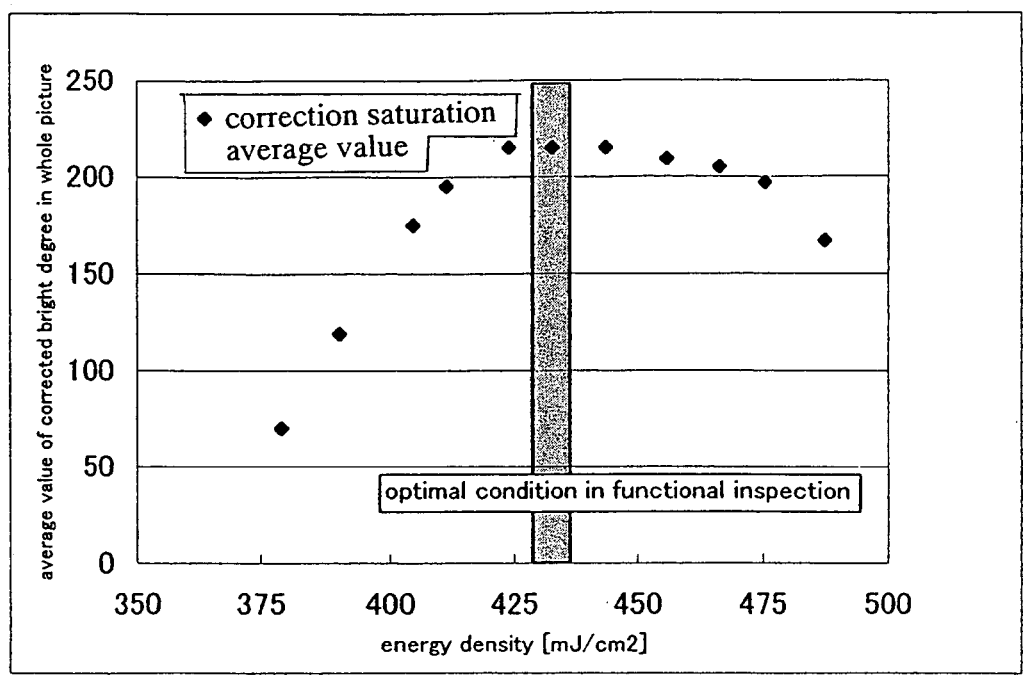
FIG. 14A ×500
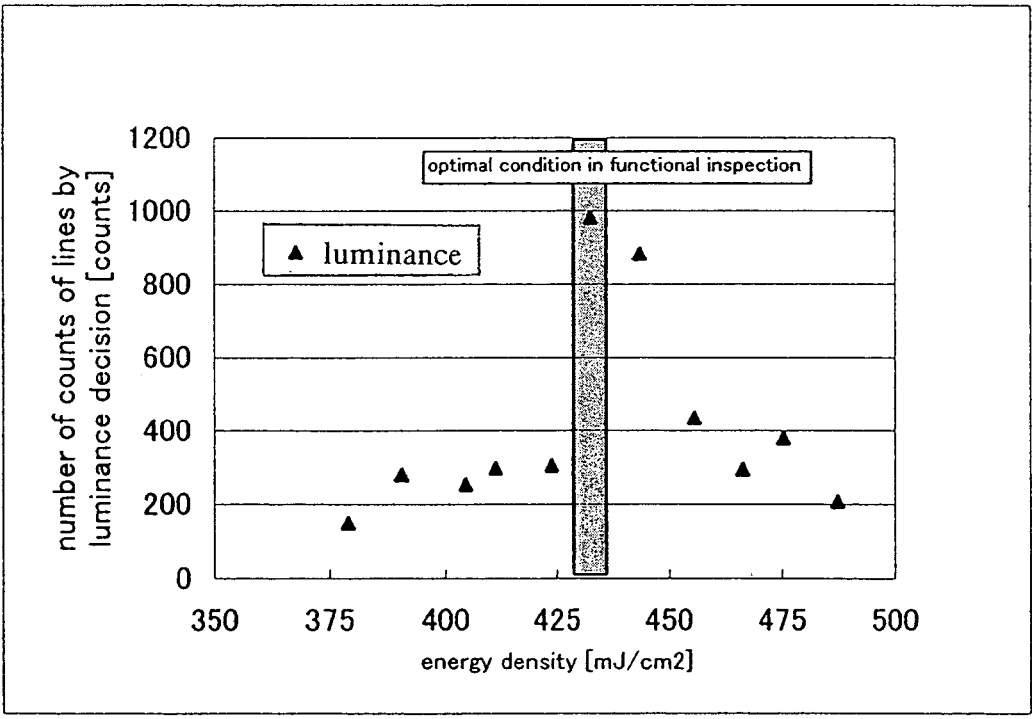
FIG. 14B ×500

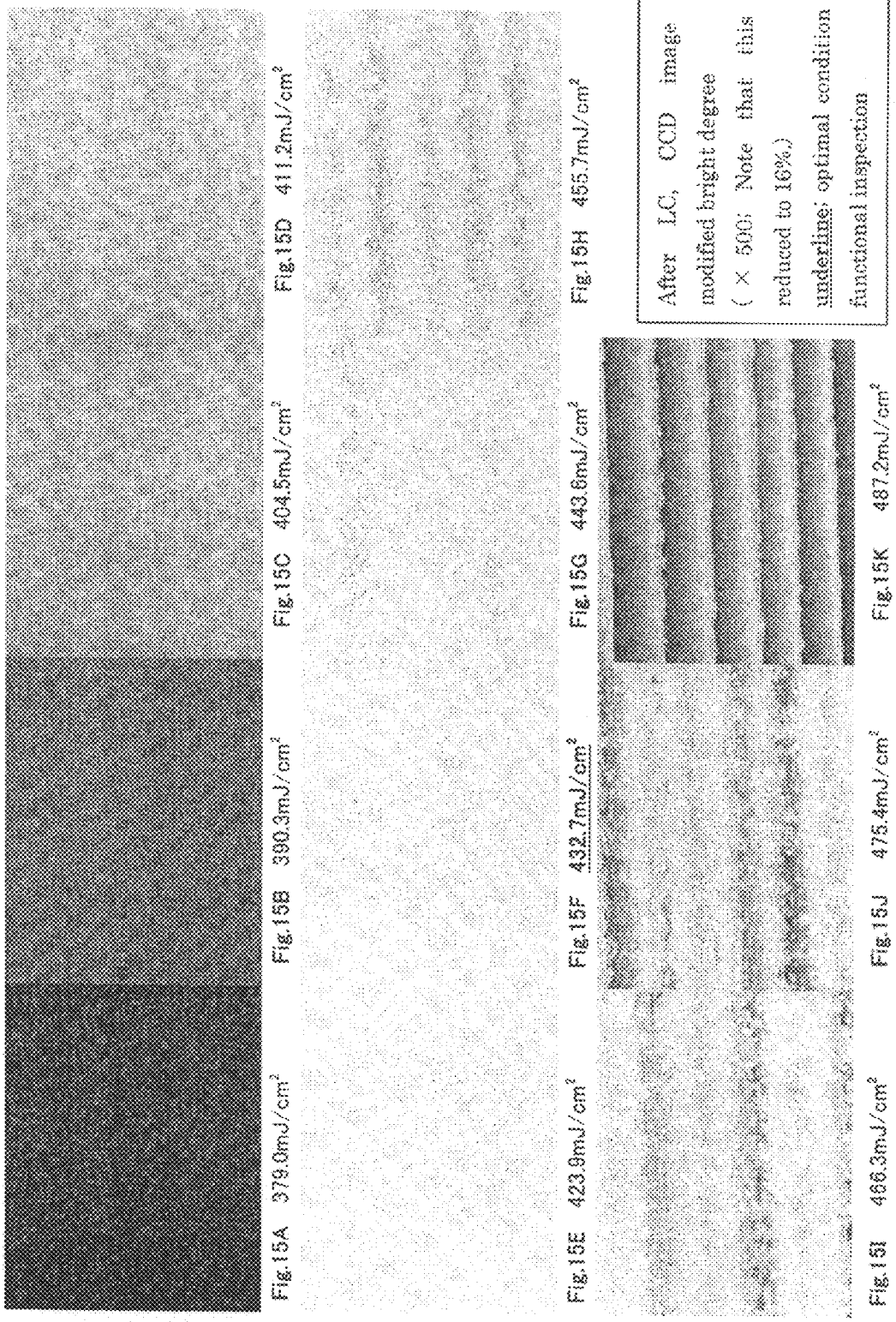

▨▨▨▨ transparent conductive film

▨▨▨▨ wring

▨▨▨▨ transparent conductive film

METHOD FOR TESTING SEMICONDUCTOR FILM, SEMICONDUCTOR DEVICE AND MANUFACTURING METHOD THEREOF

BACKGROUND OF THE INVENTION

1. Field of the Invention

The invention relates to a method for testing a crystallized semiconductor film, and more particularly such a method for testing a semiconductor film crystallized by irradiating an energy beam. The invention also relates to a device for testing a semiconductor film crystallized by irradiating an energy beam, and a manufacturing method of a semiconductor device including a step of testing a semiconductor film crystallized by irradiating an energy beam.

2. Description of the Related Art

A glass substrate is cheap and easily used in a large size as compared to a conventional single crystalline substrate. Therefore, a technology for forming a semiconductor film on a glass substrate to form a thin film transistor (hereinafter referred to as a TFT) is actively researched and advanced toward the practical use. A crystalline semiconductor film has a better TFT characteristic than an amorphous semiconductor film. As a glass substrate is weak against heat, a laser crystallization is often used for forming a crystalline semiconductor film on a glass substrate as a crystallization method which causes less thermal damage.

In the laser crystallization, a laser beam is used as an energy beam for applying energy to a semiconductor film. The semiconductor film may not be crystallized enough or micro-crystallized depending on the energy density of the laser beam to irradiate. Needless to say, crystallization is most desirably performed at an optimal energy density for crystallization; however, the optimal energy density so far was often dependent on a sensory test.

However, since the sensory test is largely dependent on the operator, quality control of the merchandise is now managed from various angles by digitalizing the crystallization condition by such as Raman spectroscopy, Atomic Force Microscope (AFM), and Total reflection X-ray Fluorescence (TXRF).

However, when the reliability and variation of the data have to be considered to obtain an accurate test result in using any of the aforementioned methods, it takes time for measurement and processing, and a server or a computer is heavily loaded when storing data for testing as the amount of required information is increased.

The optimal irradiation energy density in laser crystallization is quite unstable enough to be changed by the variation in thickness of a semiconductor film or a change in the irradiation atmosphere, further a fluctuation of the output of laser or a change of transmittance of optical system over time. Therefore, in order to perform the laser crystallization under a favorable condition, it is preferable that a substrate as a whole be tested, more preferably tested by in-situ after laser crystallization and the test result thereof be fed back promptly. However, aforementioned method takes too much time for testing, therefore, a prompt test by in-situ cannot be performed. Moreover, the testing and the setting for the optimal energy density themselves could be a delay. In that case, operating rate of the device as well as a producing capacity are drastically decreased.

A laser irradiation system generally costs high for its operation. An XeCl excimer laser used for laser crystallization in particular costs so high that the cost for one-year operation could be enough to purchase another laser irradiation system. Therefore, when the producing capacity is decreased, the cost for operation affects the price of products. It is not preferable in realizing the low price of the products.

Due to the aforementioned problems, the method for testing as described above is not practical enough to be applied to a mass production.

As a method for solving these problems, a method for obtaining a threshold of a micro-crystallization by the luminous intensity of the scattered light of an energy light irradiated on the surface of a semiconductor film after crystallization (Patent Document 1), a method for obtaining an optimal crystallization energy by digitalizing the periodicity of the recessed and projective portions by autocorrelation, which appear on the surface of a semiconductor film after crystallization (Patent Documents 2 and 3), and a method for obtaining an optimal crystallization energy by analyzing the reflected light of an ultraviolet radiation irradiated on a semiconductor film after crystallization from a refractive index or an extinction coefficient (Patent Document 4) and the like are suggested.

[Patent Document 1] Japanese Patent Laid-Open No. 2000-114174
[Patent Document 2] Japanese Patent Laid-Open No. 2001-196430
[Patent Document 3] Japanese Patent Laid-Open No. 2002-217107
[Patent Document 4] Japanese Patent Laid-Open No. 2000-31229

SUMMARY OF THE INVENTION

These and other objects, features and advantages of the present invention will become more apparent upon reading of the following detailed description along with the accompanied drawings.

Each of the suggested methods, however, also has a disadvantage in that only a threshold at which micro-crystallization occurs is obtained, an oxide film is required, and a distinct difference does not generate due to the crystallization.

In crystallizing a silicon film, a grain size becomes larger as more energy is applied; however, it becomes small rapidly when more than a certain energy is applied. This phenomena in which a crystal grain becomes small when more than a certain energy is applied is referred to as a micro-crystallization. The lowest energy at which the micro-crystallization occurs is referred to as a threshold of the micro-crystallization.

With the method for testing as disclosed in Patent Document 1 in which a threshold of the micro-crystallization only can be obtained, the lowest energy for sufficient crystallization cannot be known, therefore, the energy which does not go beyond the threshold of the micro-crystallization even when the laser output fluctuates is desirably selected. However, with the energy just below the threshold of the micro-crystallization, transformation of grain size relatively to the change in energy is quite large, thus a slight difference in the output of laser beam can change the grain size remarkably. As a change in crystal grain size is closely related to an electric characteristics of a TFT to be fabricated afterwards, it ultimately ends in the variation in TFT characteristics. The variation in TFT characteristics is a substantial problem since it is a major factor having an influence on the reliability and performance of the final products.

It is also found that the crystallization is performed with excessive energy at all times which may result in a huge loss of energy when applied to the mass production.

With the method disclosed in Patent Documents 2 and 3, crystallinity is tested by checking the shape of an oxide film formed on the surface of a semiconductor film. Here, an oxide film formed on the surface of a semiconductor film naturally (natural oxide film) cannot yield an accurate result, therefore, the natural oxide film is once removed and then a new oxide film is required to be formed for testing accurately (Patent Document 3). In the case of employing the aforementioned steps in the mass production line, it is totally disadvantageous in throughput, yield, and cost to increase these originally unnecessary steps.

Further, the method disclosed in Patent Document 4 in which there are no distinct difference between before and after the crystallization lacks reliability.

Because of the aforementioned reasons, there has been no method for testing a semiconductor film, which has a sufficient promptness, cost performance, and reliability when bringing the products using a semiconductor film which is laser crystallized into the market. The invention provides a method for testing a semiconductor film, a manufacturing method of a semiconductor film, a laser crystallization, a laser crystallization device, and a laser crystallization system which require less time for testing, have sufficient reliability, are excellent in cost management, and quite applicable to the mass production.

The invention provides a manufacturing method of a semiconductor film, a laser crystallization method, a laser crystallization device, and a laser crystallization system which enable a crystallization with an optimal crystallization energy by feeding back the result tested by the methods disclosed in this specification.

According to the invention, a crystallinity of a semiconductor film is improved by irradiating energy beam and then a visible light is irradiated on the surface of the semiconductor film of which crystallinity is improved, and the scattered light is photographed. Then, the photographed image is digitalized to obtain a digital image and the luminance of the digital image is calculated by a computer in a direction perpendicular to the scanning direction of the energy beam over the semiconductor film.

Another configuration of the invention is that a visible light is irradiated on the surface of a semiconductor film of which crystallinity is improved by irradiating energy beam and the scattered light of the irradiated visible light is photographed and digitalized to obtain a digital image. When the scanning direction of the energy beam is a Y direction and a direction perpendicular to the Y direction is an X direction in the digital image, a predetermined analysis region of the digital image is divided into m in the X direction and into n in the Y direction, thus m×n basic units are sectioned. Sum of luminance of the m basic units aligned in the X direction is calculated per each of the n rows aligned in the Y direction. An approximate line of the relation of the sum of the luminance to the corresponding alignment in the Y direction is calculated, thus the crystallinity of the semiconductor film of which crystallinity is improved is tested by the fluctuation of the sum of the luminance from the approximate line.

According to the invention, a visible light is irradiated on the surface of a semiconductor film of which crystallinity is improved by irradiating energy beam and the scattered light of the irradiated visible light is photographed and digitalized to obtain a digital image. When the scanning direction of the energy beam is a Y direction and a direction perpendicular to the Y direction is an X direction in the digital image, a predetermined analysis region of the digital image is divided into m in the X direction and into n in the Y direction, thus m×n basic units are sectioned. An average of luminance of each of the m basic units aligned in the X direction is calculated per each of the n rows aligned in the Y direction. An approximate line of the relation of the average of the luminance to the corresponding alignment in the Y direction is calculated, thus the crystallinity of the semiconductor film of which crystallinity is improved is tested by the fluctuation of the average of the luminance from the approximate line.

According to the above-described method, steps required for testing are the followings.

1. A scattered light is digitally photographed while a visible light is irradiated.
2. The photographed image is divided into basic units. (In the case where basic units are pixels, this step can be omitted.))
3. The luminance of the basic units are summed or averaged in the X direction. (This step requires only a short time since no complex calculation is required.)
4. Crystallinity is tested by a linearity or a fluctuation.

As described above, only 3 or 4 steps are required. Further, no complex operation is required in the process, therefore, a test can be quite simple. Moreover, as the amount of data to be calculated is small, it does not become a heavy load when stored and can be easily managed and handled.

According to the invention, a visible light is irradiated on the surface of a semiconductor film of which crystallinity is improved by irradiating energy beam and the scattered light of the irradiated visible light is photographed and digitalized to obtain a digital image. When the scanning direction of the energy beam is a Y direction and a direction perpendicular to the Y direction is an X direction, a predetermined analysis region of the digital image is divided into m in the X direction and into n in the Y direction, thus m×n basic units are sectioned. The case is counted as one where there are a specified number of adjacent basic units in the X direction having larger luminance than two adjacent basic units in the Y direction. Improved crystallinity of a semiconductor film is tested by the number of counts in the display.

The other configuration of the invention is that a visible light is irradiated on the surface of a semiconductor film of which crystallinity is improved by irradiating energy beam and the scattered light of the irradiated visible light is photographed and digitalized to obtain a digital image. When the scanning direction of the energy beam is a Y direction and a direction perpendicular to the Y direction is an X direction, a predetermined analysis region of the digital image is divided into m in the X direction and into n in the Y direction, thus m×n basic units are sectioned. The case is counted as one where there are a specified number of adjacent basic units in the X direction having larger luminance than two basic units apart from each other at a certain distance in the Y direction. Improved crystallinity of a semiconductor film is tested by the number of counts in the display.

That is, the luminance of the basic unit of interest ($B_{(Xn, Ym)}$) and the luminance of the adjacent (or apart from each other at a certain distance) basic units in the Y direction ($B_{(Xn, Ym-p)}$, $B_{(Xn, Ym+p)}$) are compared and the case is counted as one where the luminance of the basic unit of interest ($B_{(Xn, Ym)}$) is larger than the luminance of the adjacent (or apart from each other at a certain distance) basic unit in the Y direction ($B_{(Xn, Ym-p)}$, $B_{(Xn, Ym+p)}$), that is the case where a specified number of basic units are aligned in a row in the X direction which satisfies a condition A (($B_{(Xn, Ym)}$>$B_{(Xn, Ym-p)}$ and ($B_{(Xn, Ym)}$>$B_{(Xn, Ym+p)}$). A crystalline semiconductor film is tested by the number of counts in the display.

Furthermore, in the case where more than a specified number of basic units which satisfy the condition A are aligned in the X direction, one count may be taken when a specified number of basic units are aligned and every time one more basic unit is increased in the alignment. Or, an alignment having any number of aligned basic units may be counted as one. In the former case, when the specified number is 15, two counts are taken in the case where 16 basic units are aligned, and three counts are taken in the case of 17 basic units.

It is empirically clear in this method that the larger number the counts are, the better the crystallinity is. By comparing this number, an optimal laser energy density for laser crystallization can be obtained easily.

Furthermore, the invention requires only one value (number of count) for one energy condition to be utilized ultimately, which makes the management quite simple since a server or a computer are not heavily loaded when the data is stored.

Further, by combining with the method for obtaining the sum of the luminance in the X direction, more accurate result can be gained rather simply. This is a practical method for testing in which both operations can be performed with the same image, no complex operation is required, and each amount of data is quite small.

In the case of testing by the method for testing of the invention, TFT characteristics of the optimal laser irradiation energy density and the TFT characteristics of the energy density before and after the irradiation have little difference. Even when the energy density of laser changes slightly, a large variation hardly occurs. Thus, it is found that a good crystallinity can be obtained constantly around the optimal laser irradiation energy density region.

According to the method for testing of the invention, an irradiation energy density at which a good and stable crystallinity is obtained can be found, therefore, it is advantageous in reduction in cost of the products since excessive energy is unnecessary.

Furthermore, optimal irradiation energy for crystallization can be determined by irradiating the energy beam for crystallization to per area of a substrate or per substrate on which an amorphous semiconductor film is formed by varying the irradiation intensity, and then the method for testing of the invention is applied corresponding to each irradiation intensity.

As the method for testing of the invention has an advantageous feature as described above, a highly reliable result can be obtained simply and easily, thus the working rate of the device can be expected to be improved drastically.

Furthermore, the invention provides a unit for photographing the surface of the semiconductor film in a crystallization device so that the surface of a semiconductor film right after the crystallization can be photographed.

Thus, a semiconductor film can be tested right after the crystallization. By sensing the change in irradiation energy due to the change in output or crystallization atmosphere and rapidly feeding back the change to the irradiation energy, the irradiation energy can be modified to an appropriate density at all times.

The above-described method works efficiently with the use of the method for testing of the invention which gives a rapid result because of a simple configuration, makes a simple comparison because of small amount of data, and provides a high reliability.

Moreover, with the method and device of the invention having the above-described features, the surface of a semiconductor film right after crystallization in a laser crystallization device can be monitored in a moving picture and analyzed at all times, and a quicker feedback can be provided.

Further, the other configuration of the invention is that an average luminance of the digital image is tested together in the above-described configuration.

Further, the other configuration of the invention is that an average corrected saturation is tested together in the above-described configuration.

Further, according to the invention, more than two of the above-described methods for testing are combined for testing.

According to the invention, a substrate on which an amorphous semiconductor film is formed is irradiated with one pulse of energy beam, the surface of the substrate is irradiated with a visible light, the scattered light is photographed, the photographed image is digitalized to obtain a digital image, and the luminance of the digital image is calculated by a computer in a direction perpendicular to the scanning direction of the energy beam over the semiconductor film, thus a profile test of the energy beam is performed.

Further, according to the invention, a substrate on which an amorphous semiconductor film is formed is irradiated with one pulse of energy beam, the surface of the substrate is irradiated with a visible light, the scattered light is photographed, the photographed image is digitalized to obtain a digital image. When the minor axis of the energy beam is a Y direction and the major axis is an X direction, a predetermined analysis region of the digital image is divided into m in the X direction and into n in the Y direction, thus m×n basic units are sectioned. Sum of luminance of the m basic units aligned in the X direction is calculated per each of the n rows aligned in the Y direction. The profile testing of the energy beam is performed by a relation of the sum of the luminance to the corresponding alignment in the Y direction.

Further, the other configuration of the invention is that a substrate on which an amorphous semiconductor film is formed is irradiated with one pulse of energy beam, the surface of the substrate is irradiated with a visible light, the scattered light is photographed, the photographed image is digitalized to obtain a digital image. When the minor axis of the energy beam is a Y direction and the major axis is an X direction, a predetermined analysis region of the digital image is divided into m in the X direction and into n in the Y direction, thus m×n basic units are sectioned. An average of luminance of each of the m basic units aligned in the X directions is calculated per each of the n rows aligned in the Y direction. The profile testing of the energy beam is performed by a relation of the average of the luminance to the corresponding alignment in the Y direction.

Further, according to the invention, a laser beam is used as the energy beam in the above-described configuration.

Further, according to the invention, the visible light has such light source as a metal halide lamp, a halogen lamp, a tungsten lamp, a xenon lamp, a light emitting diode, and a fluorescent lamp.

The other configuration of the invention is that a illumination intensity of the visible light to be irradiated on the surface of the semiconductor film is 10,000 lux or more in the above-described configuration.

The other configuration of the invention is that the illumination intensity is from 20,000 to 100,000 lux in the above-described configuration.

The other configuration of the invention is that a semiconductor device using a semiconductor film which is tested by the method for testing described above in the above-described configuration is utilized.

The other configuration of the invention is that a plurality of semiconductor films which are crystallized by energy beam having a different density by the above-described method for testing are each tested and an irradiation energy density is determined by the result of the test and used for crystallization.

Further, the photographed data is tested by the saturation calculated by a special method and may be utilized instead of the luminance. In the case of utilizing the saturation, even a black color has a large saturation when using a typical calculation method to obtain a saturation, therefore, a test is performed by using HSV color system suggested by Matsuhashi etc. (The Journal of the Institute of Television Engineers of Japan, vol. 49, No. 6 pp.787 to 797). A saturation obtained by this method is quite convenient for the invention since both white and black colors have saturation levels zero. The saturation obtained by the calculation in which both white and black colors have saturation levels zero is hereinafter referred to as a corrected saturation.

Furthermore, the test by using a luminance and a method for testing by using the corrected saturation instead of luminance can be combined. Thus, more accurate result can be obtained.

According to the above-described invention, a method for testing a semiconductor film, a manufacturing method of a semiconductor film, a crystallization method, a crystallization device, and a crystallization system which require less time, have a sufficient reliability, are excellent in cost management, and quite applicable to the mass production can be provided.

Furthermore, according to the invention, a manufacturing method of a semiconductor film, a crystallization method, a crystallization device, and a crystallization system which enable crystallization with optimal energy at all times can be provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is an example of a configuration of devices according to the invention.

FIGS. 7A to 7K are images photographed by a CCD camera (×100).

FIGS. 8A to 8K are images photographed by a CCD camera (×200).

FIGS. 9A to 9K are images photographed by a CCD camera (×500).

FIGS. 10A to 10K are images photographed by a CCD camera (×500, luminance only is extracted).

Figures 13A, 13B, 13C, 13D, 13E, 13F, 13G, 13H, 13I, 13J, 13K:
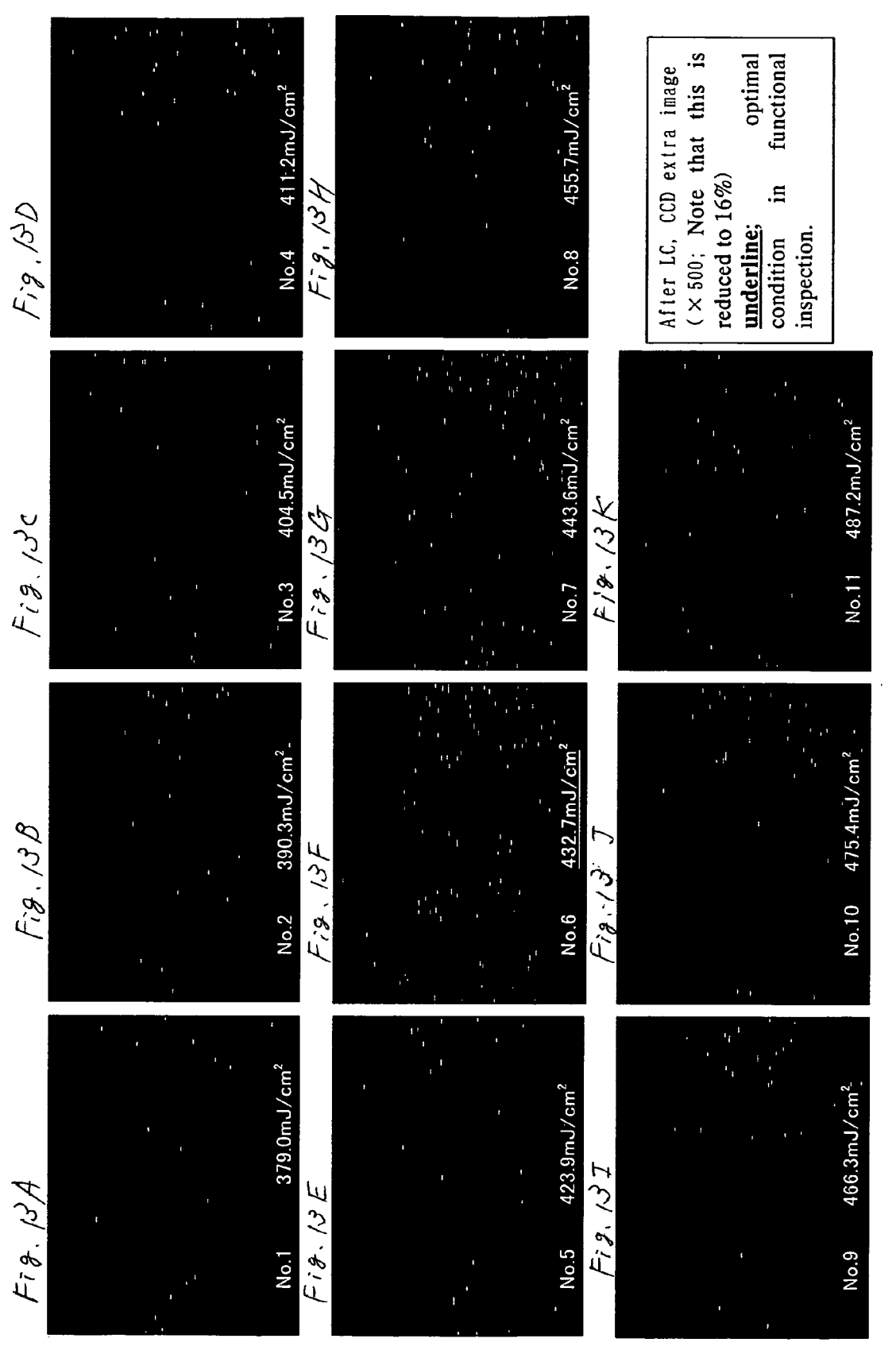

FIGS. 13A to 13K are data showing characteristic patterns and their occurrence.

FIGS. 14A and 14B show a relation between the number of the characteristic pattern and the irradiation energy density, and a corrected saturation of the image as a whole.

FIGS. 15A to 15K are images photographed by a CCD camera. (×500, corrected saturation only is extracted)

DETAILED DESCRIPTION THE INVENTION

Embodiment Mode 1

Figure 2A:
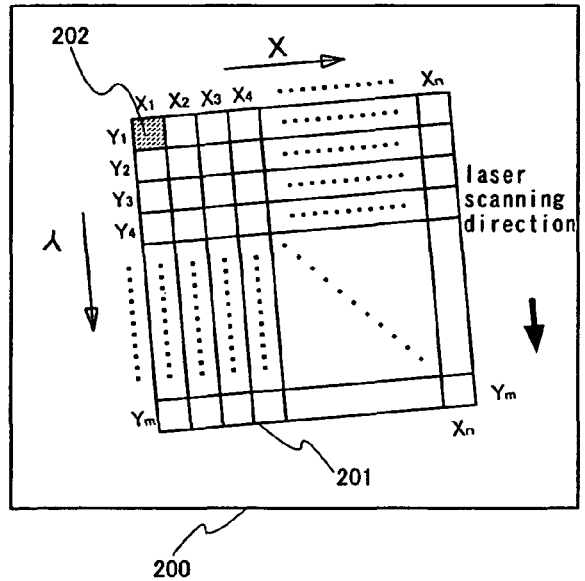
FIGS. 2A and 2B are basic image processings according to the invention.
Figure 2B:
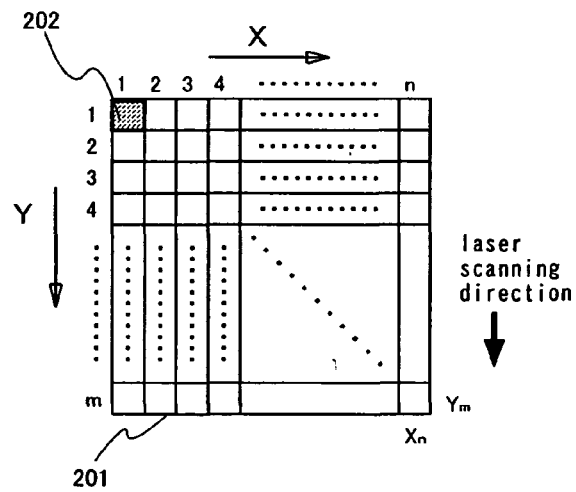

[Image processing] An image processing commonly performed in the invention is described with reference to FIGS. 2A and 2B. In an image 200 photographed by a CCD camera and the like, it is defined that a scanning direction in which a laser beam is irradiated as energy beam for crystallization is a Y direction, and a direction perpendicular to the Y direction is an X direction.

An analysis region 201 is determined by sectioning the image in a predetermined size of rectangular shape of which two sides are parallel to the X direction and the other two sides are parallel to the Y direction. Here, in the case where the X direction or the Y direction is not parallel to the side of the image, the image analysis region 201 may be rotated by using an image processing software or the like. Further, the camera may be placed so that the image and the analysis region be parallel to each other.

The analysis region is divided into n in the X direction and into m in the Y direction, as many as required. Thus, n×m basic units 202 are sectioned. In the invention, data is processed by using these basic units for analysis and testing. The luminance and a saturation of the basic units are the average or the sum of each value of the pixels in the basic units. The basic units may be the pixels of the photographed image. This case is advantageous in that the process for dividing the image can be omitted and the luminance and saturation of the basic units are already determined when the image is photographed, thus a redundant process is unnecessary.

Figure 3:
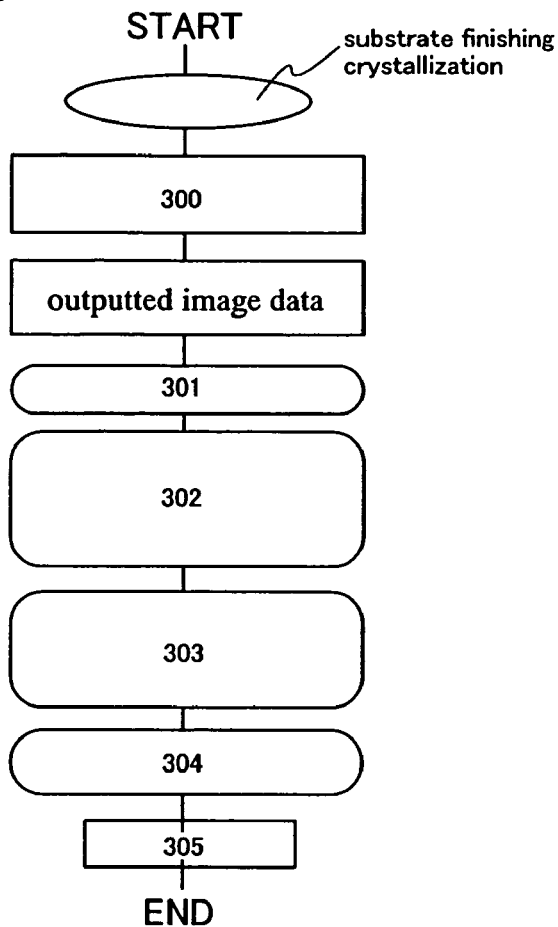
FIG. 3 is a flow chart showing the Method for testing 1.

[Method for testing 1] FIG. 3 is a flow chart showing one of the characteristic methods for testing of the invention. A substrate on which a semiconductor film crystallized by irradiating energy beam is formed (hereinafter referred to as a crystallized substrate) is photographed by a CCD camera as a dark field image (300). A dark field image is an image on which is photographed the light scattered from the irradiated object.

A metal halide lamp, a halogen lamp, a tungsten lamp, a xenon lamp, a light emitting diode, and a fluorescent lamp and the like can be used as a light for irradiation. It is one of the features of the invention that an image can be photographed by using a general light source without the use of a special light source. The light may be irradiated in any ways as long as a dark field image can be photographed by a CCD camera; however, it is preferable that a light be irradiated obliquely or a light axis be tilted by using a ring light or the like. The illumination intensity of the light is 10,000 lux or more, or more preferably 20,000 to 100,000 lux. Although magnification may be determined by an operator appropriately, a magnification of 75 to 750 times may be employed for testing the crystallinity in laser crystallization.

An image is processed according to the above-described image processing commonly performed in the invention and the analysis region is sectioned into basic units (301). Needless to say, the image and the image having a reference value for comparison are the same in magnification, shape, light, and photographing condition.

Figure 4:
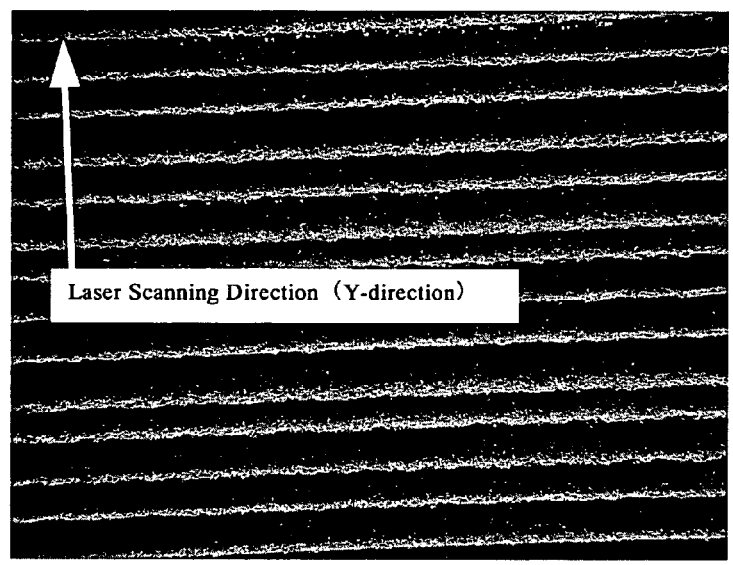
FIG. 4 shows a luminance variation.

Subsequently, an average ($Bav_{Ym}$) or a sum ($Bt_{Ym}$) of the luminance of basic units having the same Y coordinate in the analysis region is calculated. In the case of photographing a crystallized substrate in a dark field as in this embodiment mode, an image may be dark when an energy density of energy beam is not appropriate, or a luminance variation in stripe shapes (refer to FIG. 4) may appear in the direction perpendicular to the scanning direction of the energy beam (parallel to the X direction). By calculating the average or the sum of the luminance of the basic units having the same Y coordinate, that is the basic units aligned in parallel in the X direction, a luminance tendency of the row can be obtained.

By the relation of the average ($Bav_{Ym}$) or the sum ($Bt_{Ym}$) of the luminance of each Y coordinate, an approximate line is obtained (303). A fluctuation of the data is obtained (304) by this approximate line and compared with a reference value obtained in advance, thus analysis and testing are performed (305). The reference value differs depending on the performance of a semiconductor element demanded as a final product, therefore, it may be determined by an operator appropriately.

In this method for testing, the larger the average luminance of the analysis region and the smaller the fluctuation are (closer to the approximate line), that is, the smaller the variation of the luminance in the Y direction is, the better electric characteristics can be obtained when such elements as TFTs are formed.

This method for testing requires no complex operation in the process, therefore, the test can be performed quite simply. Furthermore, as the amount of data is small enough not to be a heavy load when stored, it can easily be processed and managed.

Note that in this method for testing, a corrected saturation can be utilized instead of the luminance. Further, a laser beam and the like may be employed as an energy beam here.

Figure 5A:
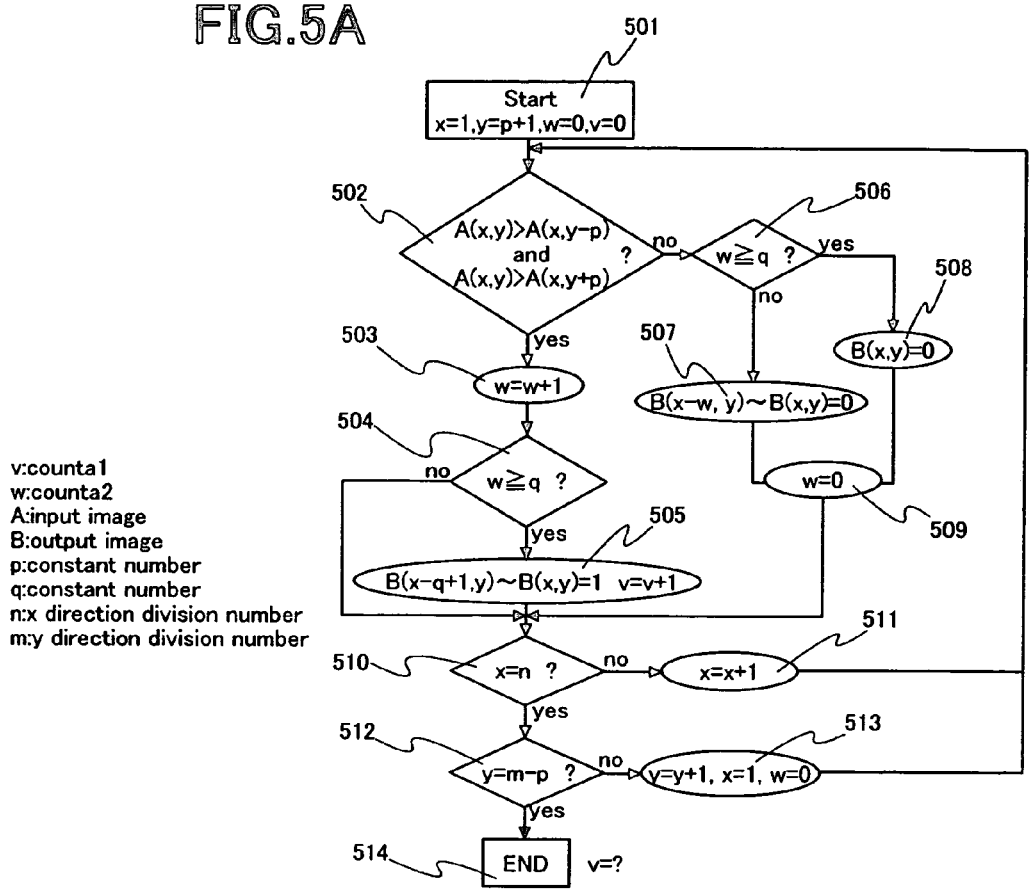
FIGS. 5A and 5B are diagrams showing Method for testing 2.
Figure 5B:
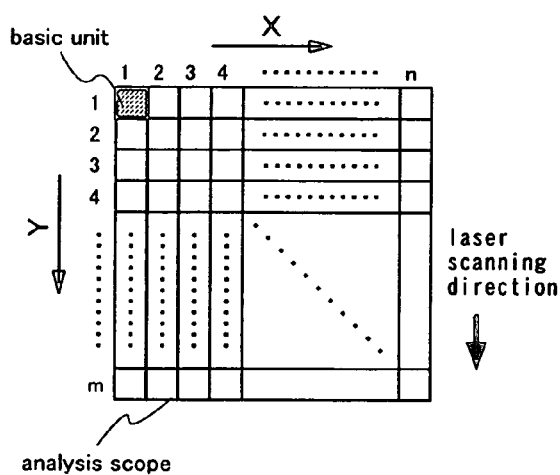

[Method for testing 2] FIG. 5A is a flow chart showing one of the characteristic methods for testing of the invention. The same process is carried out up to the photographing of the crystallized substrate and the image processing commonly performed in the invention. Or, the image which is processed in the Method for testing 1 may be utilized in the present method for testing.

This method for testing is that by extracting a characteristic pattern which appears when a crystalline semiconductor film is photographed as a dark field image, an optimal irradiation energy density is determined. The photographing method of the dark field image is the same as Method for testing 2, therefore, the description is omitted here.

The characteristic pattern is a pattern found by observing and analyzing a large number of samples by the applicants. In a sample of which crystallinity is good, thin lines which are rather lighter than the other part appear in the X direction. An example to extract this pattern is shown in the flow chart in FIG. 5A.

In order to start using this flow sheet, values shown as constant numbers have to be determined. Among them, n and m are the numbers in which the analysis region is divided in the X and Y directions in the image processing commonly performed in the invention. The numbers p and q are the values determined according to the size of the pattern relatively to the basic units. The number q corresponds to the shortest length in the X direction of the line to be recognized as a characteristic pattern, while the number p corresponds to the shortest width of the line to be recognized as the characteristic pattern. For example, when the magnification is 500 times and the number of basic units is X:Y=1200:1000 (equivalent to pixels), q=15 and p=2. These constant numbers are determined by an operator appropriately since they depend on the magnification, the size of the analysis region, and the number of basic units.

The process of the method for testing is described with reference to the flow chart shown in FIG. 5A. It should be noted that this method for testing is only an example and the invention is not limited to this. Any configuration may be structured as long as the process is carried out based on the above-described idea.

After the constant numbers are determined, the process is started as x=1, y=p+1=3, v=0, and w=0. Here, x and y are coordinates for the basic units and v and w are counters. The number v counts the pattern in line shape and w counts the number of the basic units aligned of which luminance and saturation are larger than the basic unit apart from the basic unit in process at a distance of ±p in the Y direction. The number y starts with p+1 since the luminance of the basic unit in process is compared with the basic unit at a distance of ±p in the Y direction. Further, the value of v is used for a final testing.

Subsequently, a value ($A_{(x,y)}$) such as a luminance of a basic unit in process having the coordinates of (x,y) in an input image A is compared with the corresponding value ($A_{(x,y-p)}$ and $A_{(x,y+p)}$) of the basic unit at a distance of ±p in the Y direction (502).

In the case where the value of the basic unit in process ($A_{(x,y)}$) is larger than the corresponding value ($A_{(x,y-p)}$ and $A_{(x,y+p)}$) of the basic unit at a distance of ±p in the Y direction, w is counted one (503) and then w and q are compared (504). In the case where w is equal to or more than q, a basic unit having the coordinate of (x−q+1, y) to (x, y) in an output image B is outputted as one, and the counter v is counted one (505). In the case where w is smaller than q, a next process is carried out by skipping the aforementioned process.

In the case where the value of the basic unit in process ($A_{(x,y)}$) is smaller than the corresponding value ($A_{(x,y-p)}$ and $A_{(x,y+p)}$) of the basic unit at a distance of ±p in the Y direction, w and q are compared immediately (506). In the case where the value of w is smaller than q, a basic unit having the coordinate of (x−w, y) to (x, y) is outputted as zero (507). Further, in the case where w is equal to or more than the value of q, B (x, y) is outputted as zero (508). In both cases, the counter w is reset to zero (509).

Once the process for comparing the luminance and the like is terminated, an x coordinate of the basic unit in process is checked (510). In the case where x is not n, x is added one (511) and returns to the first process with both w and v processed. In this case, the value of y is not changed. In the case where x=n is satisfied by repeating the aforementioned process, the value of y is checked (512). In the case where the value of y is not m−p, y is added one, x is reset to one and w is reset to zero (513), then returns to the first process. Then, the process as described above is carried out, and the process for one analysis region is terminated when y=m−p is satisfied (514). The result utilized for testing is the value of v; however, the output image B may be displayed or printed out if required.

The value of v obtained as described above is compared with the predetermined reference value for analysis and testing. The reference value differs depending on the performance of a semiconductor element demanded as a final product, therefore, it may be determined by an operator appropriately. According to the research made by the present applicants, a larger value of v which is the number of the characteristic patterns indicates the better crystallinity.

This method for testing requires the process of only a comparison, addition and subtraction of the values, therefore, it takes comparatively short period of time. Further, as the test ultimately requires the value of v only, it is advantageous in that the quality control by comparing with the other data and storing the data is easy since the amount of data is small. Moreover, in the case of displaying and storing the result of process as an image, the output image B is expressed as a binary of 0 and 1, therefore, the amount of data can be comparatively small. With this data form, the data can be further small by run length encoding.

It should be noted that the corrected saturation can be utilized instead of the luminance in this method for testing.

[Method for testing 3] A more reliable test can be performed by using Methods for testing 1 and 2 in combination.

In Methods for testing 1 and 2, the same CCD image can be utilized and both methods have features that analysis is simple and the amount of data is small. Therefore, by using both methods in combination, reliability can be improved without increasing the process time and the load on the server much.

Furthermore, an average luminance of the image and data of saturation can be used altogether or combined appropriately for testing. Thus, a more reliable testing can be performed from various aspects.

It is one of the features of the method for testing of the invention that the surface of a crystallized semiconductor film is photographed in a dark field image. Due to the characteristics of a camera or the photographic condition and light condition, the photographed image may have a variation in luminance on the same image. In that case, a white level calibration plate may be used for photographing before the photographing for testing, and then correction may be carried out according to the obtained value.

It should be noted that the corrected saturation can be utilized instead of the luminance in this method for testing.

Embodiment Mode 2

Figure 6:
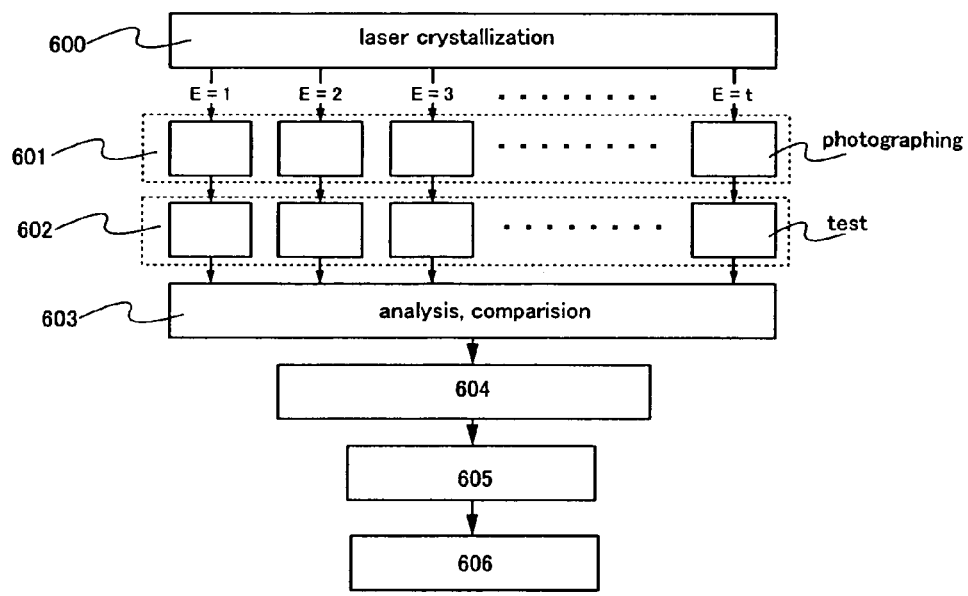
FIG. 6 is a diagram showing a method for determining an energy density of a laser irradiation for crystallization.

In this embodiment mode, a method for determining the irradiation energy density of an energy beam irradiation device by using the method for testing of the invention is described with reference to FIG. 6.

A substrate on which an amorphous semiconductor film is formed is irradiated for crystallization with an energy beam by changing the irradiation energy density (600) (irradiation energy density: E=1 to t). The energy density of the energy beam may be changed for each substrate or each sectioned area of the substrate.

Subsequently, each of the semiconductor films crystallized by each irradiation energy density is photographed by a CCD camera (601), and tested by the method described in the Methods for testing 1 to 3 (602). Values calculated after the analysis are compared to each other in their energy density (603) and the optimal crystallization energy density as seems best is determined (604). The optimal crystallization energy density as seems best is a condition in which a fluctuation is small in the case of Method for testing 1, a condition in which the value of v is large in the case of Method for testing 2, and in the case of Method for testing 3, the largest average luminance and corrected saturation may be selected.

After that, the energy beam irradiation device is set (605) so that the crystallization is performed at a determined crystallization energy density, then the crystallization of a substrate as a product is started (606).

According to the method of this embodiment mode, the optimal irradiation energy density which has been determined by a sensory test can be determined by an image processing and calculation by a computer. Thus, it is less dependent on operators, a server and a computer are not heavily loaded even when information is stored since each state is converted into simple values, and it is advantageous in the quality control of the products.

The calculation is not complex and can be terminated in a short period of time, thus the time required for testing can be reduced. The optimal irradiation energy density can be determined with an approximate focus, therefore, a substrate is not crystallized with an excess energy, and an excellent cost performance can be realized. It is thus found that this method is practical enough to be applied to mass production.

The energy beam in this embodiment mode can employ a known energy beam such as a laser beam.

Embodiment Mode 3

FIGS. 7 to 15 show the results of the measurement and testing of a substrate crystallized by actually using a laser beam. FIGS. 7 to 9 are dark field images photographed by a CCD camera. FIGS. 7A to 7K show 100 times magnification, FIGS. 8A to 8K show 200 times magnification, and FIGS. 9A to 9K show 500 times magnification image, each of which are reduced views in 16%. The actual testing was performed by analyzing the images of 100, 200, and 500 times magnification before the reduction in 16%. The laser irradiation energy density of each of the images No. 1 to 11 is shown in the following table 1.

[Table 1]

TABLE 1

| Image No. | energy density [mJ/cm2] |
|---|---|
| 1 | 379 (−12.40%) |
| 2 | 390.3 (−9.80%) |
| 3 | 404.5 (−6.52%) |
| 4 | 411.2 (−4.97%) |
| 5 | 423.9 (−2.03%) |
| <u>6</u> | <u>432.7 (±0)</u> |
| 7 | 443.6 (+2.519%) |
| 8 | 455.7 (+5.32%) |
| 9 | 466.3 (+7.77%) |
| 10 | 475.4 (+9.87%) |
| 11 | 487.2 (+12.60%) | underline: image regarded as optimal

When these images are tested by a sensory test, an image of which irradiated energy density seems optimal is No. 6 in the case of 100 and 200 times magnification, and No. 5 in the case of 500 times magnification. Table 2 shows the best three results of the sensory test of each magnification.

[Table 2]

TABLE 2

| Ranking | Magnification | | |
|---|---|---|---|
| | ×100 | ×200 | ×600 |
| 1 | <u>No. 6</u> | <u>No. 6</u> | No. 5 |
| 2 | No. 5 | No. 5 | <u>No. 6</u> |
| 3 | No. 7 | No. 7 | No. 7 | underline; image regarded as optimal

As shown, the first to third of any magnification are either No. 5, 6, or 7. It is also clear from FIGS. 7 to 9 that there is no large difference. In this case, the optimal laser irradiation energy density tends to change depending on the operator of the sensory test, which is not preferable in the factory where the quality of products are required to be maintained. Further, it takes a lot of time and trouble to take out the crystallized substrate, prepare the substrate for the observation by a microscope, observe it, and achieve the result.

Subsequently, testing is carried out by Method for testing 1 of the invention. In Method for testing 1, a luminance value of each image is utilized. Images of extracted luminance of the images in 500 times magnification according to FIGS. 8A to 8K are shown in FIGS. 10A to 10K as a reference.

Testing is carried out in the images of FIGS. 7A to 7K (100 times magnification), FIGS. 8A to 8K (200 times magnification), and FIGS. 9A to 9K (500 times magnification). X directions of the images are oblique to the display, therefore, the X direction and the alignment of the pixels are aligned by using an image processing software in advance. The pixels are used as basic units.

Figure 11A:
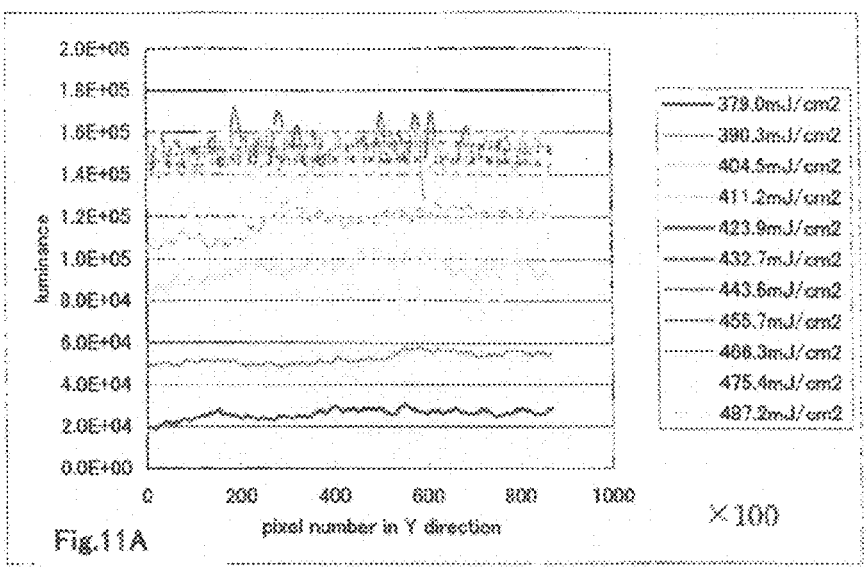
FIGS. 11A to 11C are graphs of luminance shown two dimensionally in Y direction.
Figure 11B:
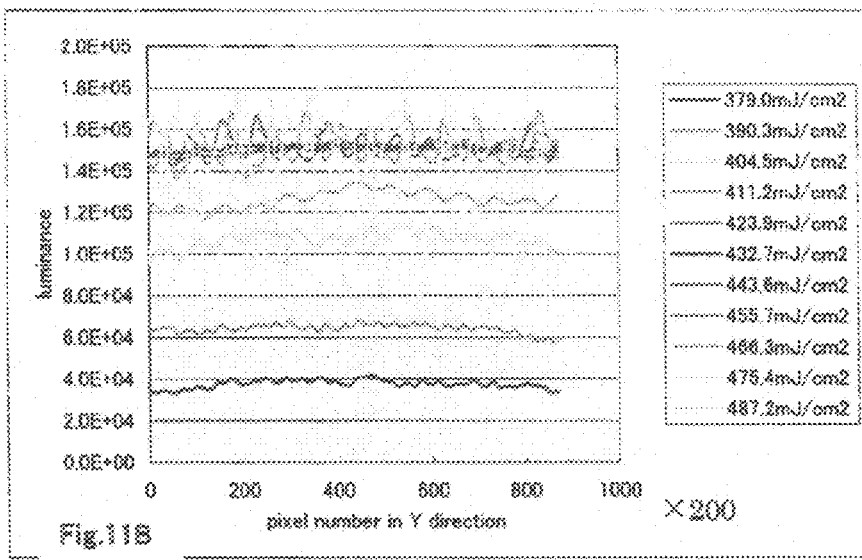
Figure 11C:
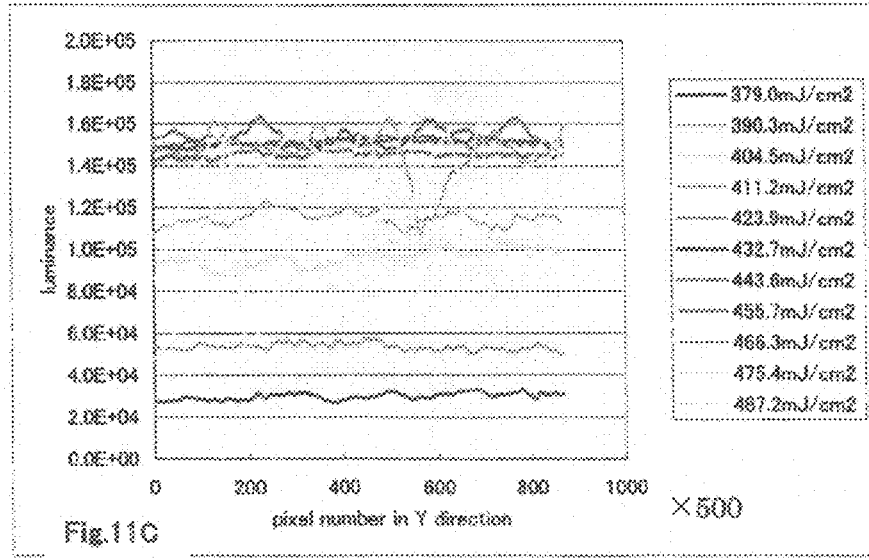

FIGS. 11A to 11C are graphs of the luminance shown two dimensionally in Y direction by using Method for testing 1 before obtaining an approximate line and fluctuation. The images considered as optimal by a sensory test are No. 6 or 5. On the basis of this result, it can be found from FIGS. 11A to 11C that the luminance of the image is decreased as an energy density gets smaller apart from the optimal laser irradiation energy density, while the luminance of the image increases as the energy density gets larger apart from the optimal laser irradiation energy density.

Figure 12A:
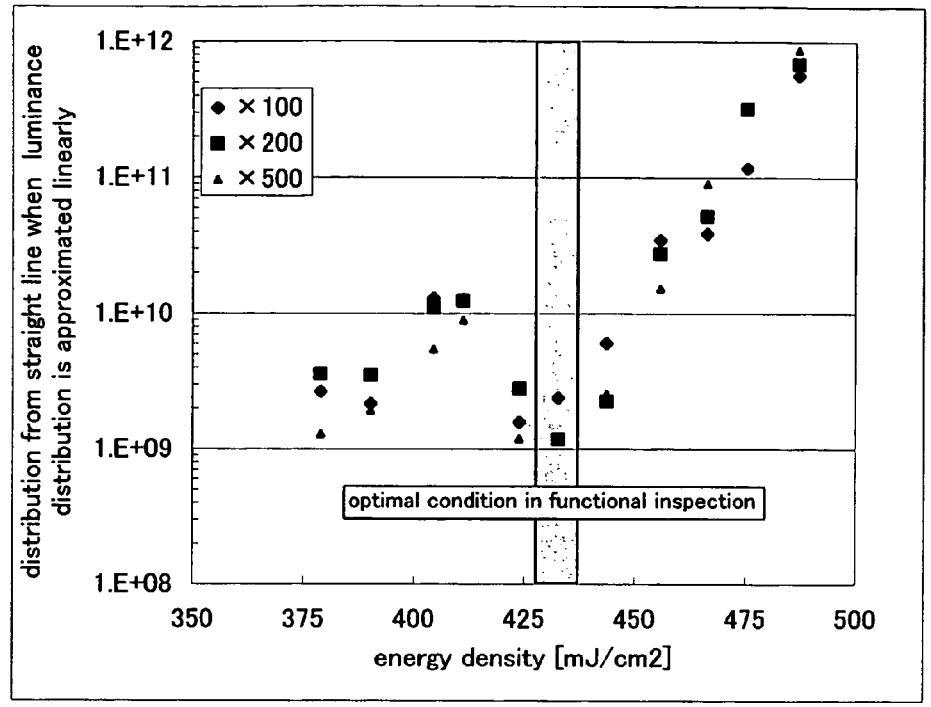
FIGS. 12A and 12B show a fluctuation from an approximate line and an average luminance of an image as a whole in the graph of luminance shown two dimensionally in Y direction.

FIG. 12A is a graph on which a fluctuation obtained from an approximate line of each data shown in FIGS. 11A to B are plotted against a corresponding laser irradiation energy density of each image. The fluctuation is approximately at the lowest level around under the optimal condition found by a sensory test, thus the optimal laser irradiation energy density can be determined.

The results of Method for testing 1 is shown in Table 3.

[Table 3]

TABLE 3

| Ranking | Magnification | | |
|---|---|---|---|
| | ×100 | ×200 | ×500 |
| 1 | No. 5<br>Iave = 147092.37,<br>$\chi^2$ = 1576137067.69 | No. 6<br>Iave = 150773.21<br>$\chi^2$ = 1183441246.96 | No. 6<br>Iave = 150750.69<br>$\chi^2$ = 1136033157.57 |
| 2 | No. 6<br>Iave = 152666.57<br>$\chi^2$ = 2380243804.95 | No. 7<br>Iave = 151851.67,<br>$\chi^2$ = 2251576505.41 | No. 5<br>Iave = 144950.20<br>$\chi^2$ = 1198144579.60 |
| 3 | No. 7<br>Iave = 153714.22<br>$\chi^2$ = 6024570507.37 | No. 5<br>Iave = 149289.91<br>$\chi^2$ = 2791476021.76 | No. 7<br>Iave = 151951.89<br>$\chi^2$ = 2561081865.95 |

Average value and variation degree are shown in a parenthesis.

TABLE 4

| Image No. | average value of modified bright degree in whole image | number of lines (luminance) |
|---|---|---|
| No. 7 | 215 | 884 |
| No. 6 | 215 | 981 |
| No. 5 | 215 | 306 |

(×500)

Every result shows that No. 5 or 6 is an optimal condition, which means the test can be performed at the same precision as the sensory test.

Thus, according to the invention, an optimal laser irradiation energy density which has been tested by a sensory test so far can be found by an image processing and calculation by using a computer. It is quite advantageous in that it is less dependent on operators, a server and a computer are not heavily loaded when information is stored since each state is converted into simple values, thus the quality of the products can be controlled easily.

The calculation is not complex and can be terminated in a short period of time, thus the time required for testing can be reduced.

Figure 12B:
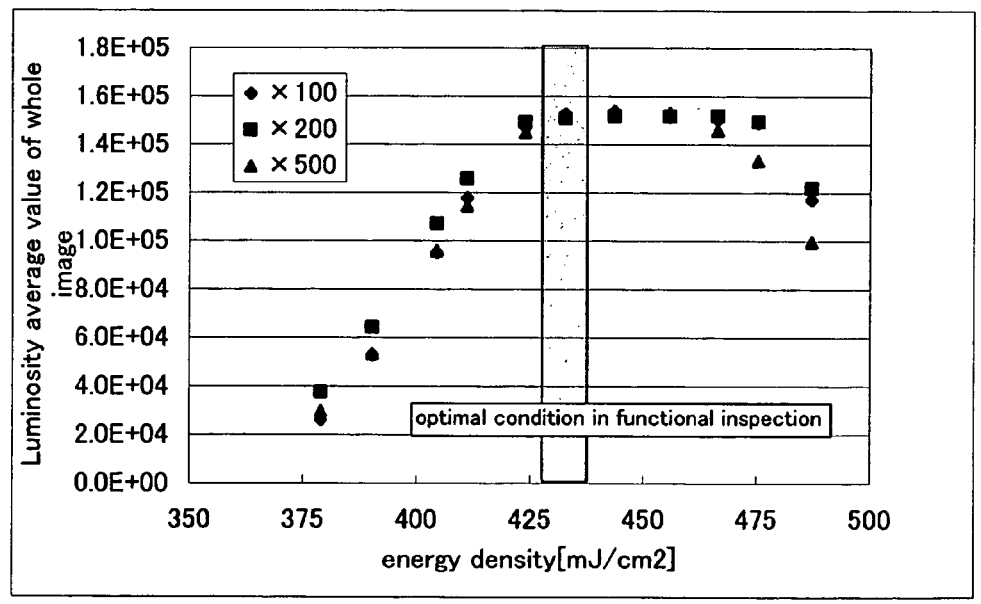

FIG. 12B is a graph on which an average luminance of each image is plotted against a corresponding laser irradiation energy density of each image. It can be found that the graph showing a relation between the average luminance and the laser irradiation energy density has a convex shape with a flat top indicating an approximately the best luminance of the optimal laser irradiation energy density.

This graph shows that the change in luminance is small around under the optimal condition. As it is hard to tell which is the optimal condition in this graph, the average luminance may be used in combination with the aforementioned method for obtaining the fluctuation or a method for extracting a characteristic pattern.

As an example, a combination of the average luminance and the method for obtaining a fluctuation according to Method for testing 1 is described. FIG. 12A which shows the result of Method for testing 1 shows that the fluctuation is comparatively small even in the region where the irradiation energy density is small even though it has the smallest fluctuation around under the optimal condition found by the sensory test. By using the average luminance in combination, more accurate testing can be carried out with a condition having a large luminance and a small fluctuation according to Method for testing 1 as an optimal laser irradiation energy density.

FIG. 14A is a graph made by using an average corrected saturation instead of the average luminance. FIGS. 15A to 15K show an image which extracted only a corrected saturation in FIGS. 9A to 9K. It can be found in FIGS. 15A to 15K that around No. 6 which is found optimal by a sensory test shows the largest corrected saturation. Therefore, more accurate testing can be carried out by using the average corrected saturation in combination with Method for testing 1, as well as the aforementioned method by using the average luminance.

FIGS. 13A to 13K show the extracted images outputted after an image processing by using Method for testing 2. An image photographed in 500 times magnification is shown in a reduced view of 20%. The measurement and processing are carried out under the condition of 500 times magnification and the number of basic units is X:Y=1200:1000 (equivalent to pixels), and q=15 and p=2. Note that in this processing, the extracted pattern is shown in white and the other part is shown in black.

It is found that quite a number of patterns (shown as white lines) appear at the laser irradiation energy density around under the condition found optimal by the sensory test. The number of these lines are counted and plotted against the corresponding laser irradiation energy density of each image on a graph in FIG. 14B. It is obvious from this graph that the number of patterns is large especially around under the laser irradiation energy found as optimal by the sensory test.

Thus, the optimal laser irradiation energy density can be presumed by extracting and counting a characteristic pattern which appears after laser crystallization. Thus, the optimal laser irradiation energy density which has been tested by a sensory test so far can be found by an image processing and calculation by a computer. It is quite advantageous in that it is less dependent on operators, a server and a computer are not heavily loaded when information is stored since each crystallization state is converted into simple values, thus the quality of the products can be controlled easily.

The calculation is not complex and can be terminated in a short period of time, thus the time required for testing can be reduced.

Furthermore, more accurate testing can be carried out by using an average luminance or an average corrected saturation of the image in combination as was in Method for testing 1. It is also preferable to use in combination with Method for testing 1 to improve the reliability. It is needless to say that using two or more of these methods can further improve the accuracy and reliability. All of the method for testing according to the invention can be carried out easily by using a computer, therefore, using these methods in combination does not waste much time.

Embodiment Mode 4

In this embodiment mode, a method for performing a good laser crystallization at all times by feeding back the result of the testing right after the laser crystallization is described.

A laser, an excimer laser in particular tends to have a fluctuation in its output and a transmittance of optical system over time. Therefore, it is sometimes the case that an energy density irradiated on a substrate changes over the operation even though an optimal laser irradiation energy density is set in advance. Thus, it is preferable that all the crystallized substrates or a determined number of the substrates be tested and the results be fed back for controlling the irradiation energy density sequentially.

FIG. 1 shows an example of a schematic view of a laser crystallization system. A part framed with a dotted line (i) is a device used for testing, and the other parts are devices used for laser crystallization. A laser beam irradiated from a laser oscillator 1601 controls an energy density by passing through an attenuator (ATT) 1602 for controlling a laser irradiation density, and formed in a desired shape by passing through an optical system 1603.

An optical system employing a configuration set forth in Unexamined Patent Publication Hei 8-195357 and the like has a good processing efficiency when its laser beam is processed into a linear shape. The laser beam which is processed into a desired shape is irradiated on a substrate 1604 on which amorphous semiconductor film is formed and laser crystallization is performed. A stage 1605 where the substrate 1604 is set up can move to an X direction and a Y direction, and a laser is scanned by moving the stage. A method for scanning the laser is not limited to this, but an assembly for scanning a laser beam by providing a mirror which is capable of changing the angle of laser irradiation can be used, or the invention is not limited to this as long as the laser beam can be irradiated on a substrate adequately.

The substrate 1604 is crystallized from the location where the laser beam is irradiated. Provided that a CCD camera 1606 for photographing a crystallized substrate is provided in an irradiation chamber 1607 for irradiating a laser on a substrate as shown in FIG. 1 so that a testing can be performed as soon as the crystallization is performed, a fairly quick response can be achieved corresponding to the change of crystallization due to the change in condition. As an ultimate idea, when the CCD camera is placed obliquely as a CCD camera shown wiuth a dotted line shown in the figure, testing can be performed as quickly as possible after the crystallization process.

An image photographed by the CCD camera 1606 is transmitted to an operation and data storage computer 1608 to be tested according to Methods for testing 1 to 3. A reference is determined in advance so that a desired performance for applications can be obtained appropriately. In the case where the result of the testing does not match the reference, a control computer 1609 controls the outputs of an laser oscillator 1601 and/or an ATT controller 1610.

According to this embodiment mode, an image is photographed and the result of the testing is fed back right after crystallization. Therefore, the time required until the result is reflected can be short. With a reference determined well in advance, defects due to the variation in laser output or an optical system over time can be avoided.

Figure 16A:
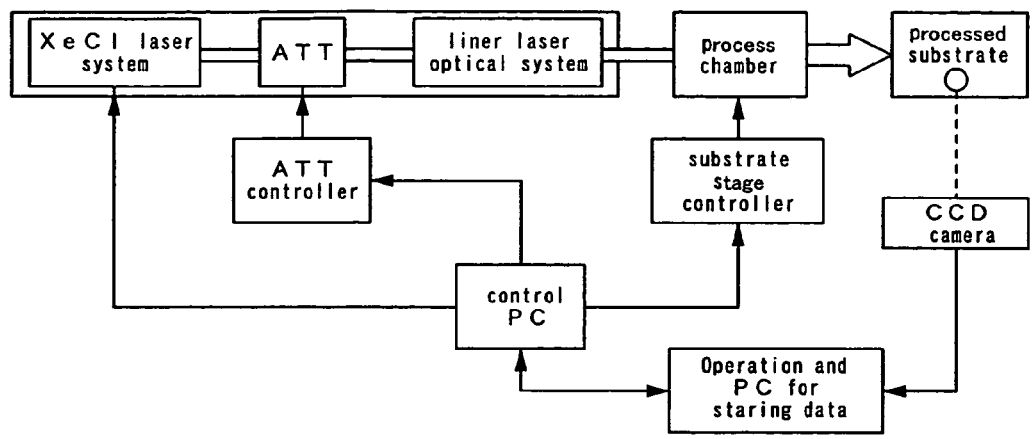
FIGS. 16A and 16B are block diagrams showing a laser crystallization system.
Figure 16B:
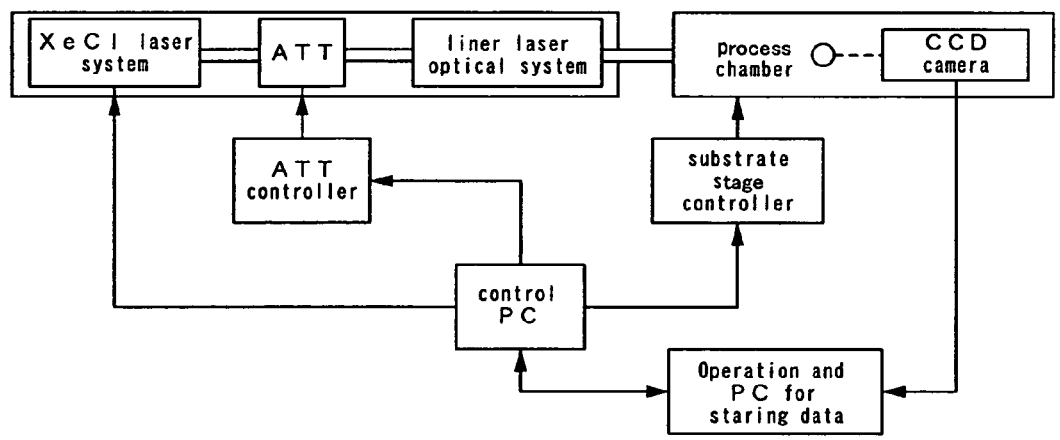

An example in which an image is photographed by the CCD camera in the irradiation chamber right after the laser irradiation as shown in FIG. 16B, however, the image may be photographed outside the irradiation chamber as shown in FIG. 16A. It should be noted that it is preferable that the time for photographing and testing after crystallization be as short as possible in the case of feeding back the result. Thus, this embodiment mode is fairly preferable.

An image 1600 is an enlarged perspective view of the periphery of the CCD camera 1606 and the light. A pattern diagram using a ring light 1611 is shown as an example of photographing a dark field image. The dark field image may be photographed by a known method and not limited to this. It is preferable to use the ring light in the case of providing it in the laser irradiation chamber as in this embodiment mode since a device for photographing can be structured simply and the light can be irradiated uniformly. Note that the CCD camera 1606 is configured with a CCD element, a zoom lens, and a field lens. An image is photographed by attaching the ring light to the CCD camera.

According to this embodiment mode, a change of crystallization due to the variation in optical system over time can be sensed quickly and fed back, therefore, the yield of the products can be improved. Such a quick feedback can only be realized by a method for testing of the invention which does not require a complex calculation and a result can be obtained quickly and correctly.

It is also possible to manage more accurately by photographing a moving image and testing it sequentially. A moving image is composed of still pictures, therefore, the invention can be applied without any change.

Embodiment 1

Figure 17A:
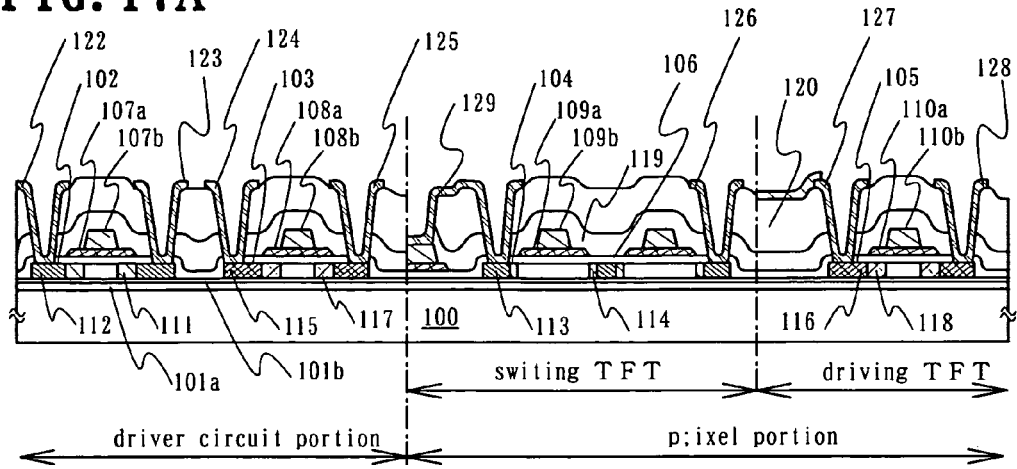
FIGS. 17A and 17B are diagrams showing an embodiment of the invention.
Figure 17B:
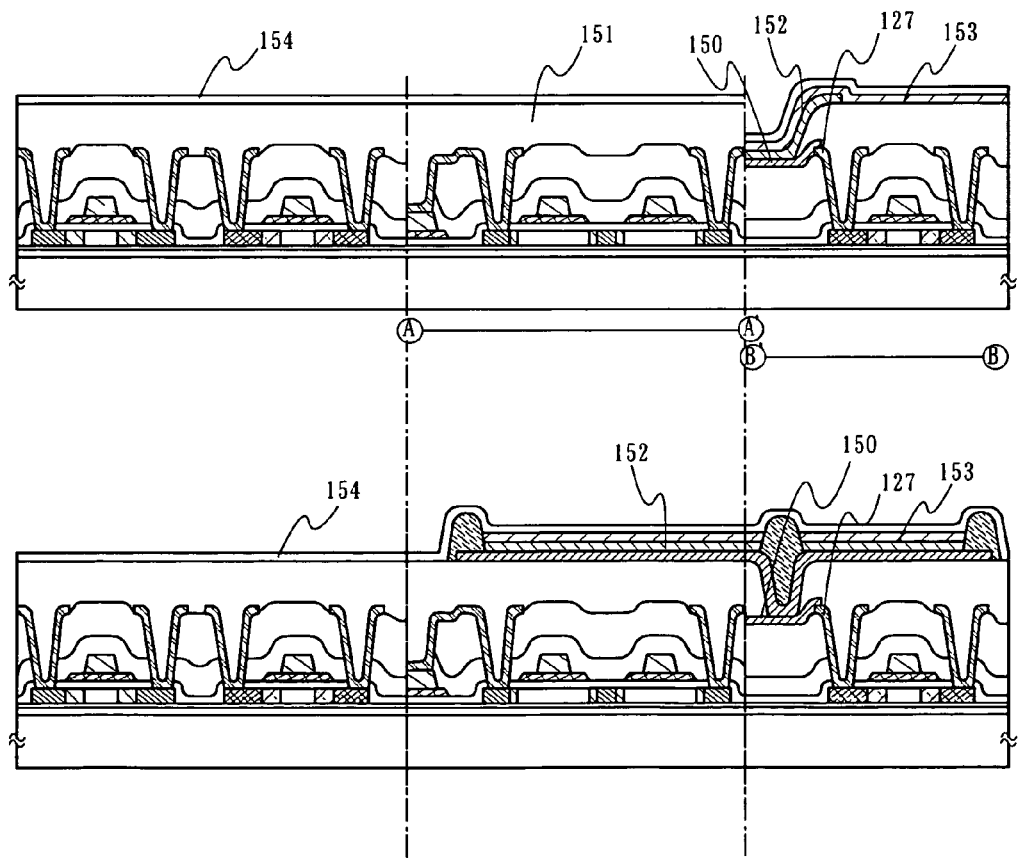

In this embodiment, description is made on the process in which an optimal laser irradiation energy density is determined, a crystalline semiconductor film is formed as a product, and a testing is performed to make a semiconductor device with reference to FIGS. 17A and 17B.

Base insulating layers 101a and 101b are formed on a substrate 100 which is used as an actual product. The substrate 100 may be a glass substrate, a quartz substrate, an insulating substrate such as a crystalline glass, a ceramic substrate, a stainless substrate, a metal substrate (tantalum, tungsten, molybdenum and the like), a semiconductor substrate, a plastic substrate (polyimide, acryl, polyethylene terephthalate, polycarbonate, polyarylate, polyethersulfone and the like), or a substrate which can resist the heat generated in the process. A glass substrate is used in this embodiment.

The base insulating layers 100a and 100b are formed by a single layer or lamination of two or more of insulating films such as a silicon oxide film, a silicon nitride film, and a silicon oxynitride film. These films are formed by using a known method such as sputtering, a low pressure CVD, and plasma CVD. This embodiment employs a lamination of two layers; however, a single layer or a plurality of layers of three or more layers may be employed as well. In this embodiment, an insulating layer 100a as a first layer is formed of a silicon nitride oxide film of 50 nm in thickness, and an insulating layer 100b as a second layer is formed of a silicon oxynitride film of 100 nm in thickness. It should be noted that the silicon nitride oxide film and the silicon oxynitride film are different in the proportion of nitrogen and oxygen. The former has more nitrogen than the latter.

Subsequently, an amorphous semiconductor film is formed. The amorphous semiconductor film may be formed by silicon or a silicon-based material (for example $Si_xGe_{1-x}$ and the like) of 25 to 80 nm (preferably 30 to 60 nm) in thickness. As a fabricating method, a known method such as sputtering, low pressure CVD method, plasma CVD method and the like may be used. In the present embodiment, the amorphous semiconductor film is formed of amorphous silicon of 50 nm in thickness.

Subsequently, the amorphous silicon is crystallized. In this embodiment, the semiconductor film is doped with an element for promoting crystallization, heated to be crystallized, and then crystallized by laser.

A thin layer containing nickel is formed on the surface of a semiconductor film by applying by a spinner a nickel acetate solution or a nickel nitrate solution containing nickel in a concentration of 5 to 10 ppm in terms of weight. The nickel element may be scattered on the whole surface of the semiconductor film by sputtering instead of applying by spinner. As a catalytic element, one or a plurality of the elements such as iron (Fe), palladium (Pd), tin (Sn), lead (Pb), cobalt (Co), platinum (Pt), copper (Cu), gold (Au) may be used as well as nickel (Ni).

Subsequently, the amorphous semiconductor film is crystallized by heating. It may be carried out at a temperature of 500 to 650° C. for about 4 to 24 hours since a catalytic element is used. The semiconductor film is crystallized by this crystallization process.

Then, the semiconductor film is crystallized by laser to improve the crystallinity. As a laser oscillation device, a pulse oscillation or a continuous oscillation gas or solid state and a metal laser oscillation device may be used. As a gas laser, excimer laser, Ar laser, Kr laser and the like may be used, while as a solid state laser, YAG laser, $YVO_4$ laser, $GdVO_4$ laser, YLF laser, $YAlO_3$ laser, glass laser, ruby laser, alexandrite laser, sapphire laser may be used, and as a metal laser, helium cadmium laser, copper steam laser, gold steam laser may be used. As a crystal of laser medium of a solid state laser, one or a plurality of the elements $Cr^{3+}$, $Cr^{4+}$, $Nd^{3+}$, $Er^{3+}$, $Ce^{3+}$, $Co^{2+}$, $Ti^{3+}$, $Yb^{3+}$, or $V^{3+}$ is doped as an impurity.

A laser oscillated from a laser oscillation device may be irradiated in a linear shape by using an optical system. The linear laser can be obtained by using a typical cylindrical lens or a concave mirror. The laser may be irradiated with the power density in the range of 0.01 to 100 $MW/cm^2$ in the atmosphere or an atmosphere of which oxygen concentration is controlled, an $N_2$ atmosphere, or in vacuum. Further, in the case of using a pulse oscillation laser, it is preferable that the laser energy density be 100 to 1500 $mJ/cm^2$ (representatively 200 to 500 $mJ/cm^2$) with a frequency of 30 to 300 Hz. The laser beam may be irradiated while overlapping by 50 to 98% by calculating with FWHM. Note that the crystallization is carried out in an atmosphere in the present embodiment.

A substrate is sectioned into stripes under the aforementioned conditions to be crystallized by a laser with different energy density according to each area. The energy density may be changed according to each substrate although it is changed according to each area in this embodiment.

A crystallized substrate is sequentially photographed by a CCD camera and the photographed data is inputted to an calculation and data storage computer. The computer tests the inputted data by the aforementioned methods described in Embodiment Modes 1 to 5 and determines an optimal laser irradiation energy density for crystallization. In the case where FIG. 12A corresponds to the result of Method for testing 1, FIG. 14B corresponds to the result of Method for testing 2, FIG. 12B corresponds to the average luminance obtained by multiple testing of Method for testing 3, and FIG. 14A corresponds to the corrected saturation, for example, it is found comprehensively that the image No. 6, that is the irradiation energy density 432.7 $mJ/cm^2$ is the optimal energy density under the aforementioned conditions.

The optimal irradiation energy density is inputted from the calculation and data storage computer to a control computer. The control computer controls the laser oscillation device and the ATT controller so that the laser is irradiated at the optimal laser irradiation energy density.

A substrate as a product is crystallized with the optimal laser irradiation energy density. After an insulating layer is formed on a substrate and the substrate is crystallized as in the case with the substrate used for determining the optimal laser irradiation energy density, the substrate is photographed right after the crystallization, tested and monitored at all times as in Embodiment Mode 4. Thus, testing of the crystalline semiconductor film, monitoring and feedback of the change in laser irradiation energy condition may be carried out.

A substrate determined to be "good" only proceeds to the subsequent step.

The semiconductor film crystallized by using a metal for promoting the crystallization as in this embodiment contains the metal element in the film. As this residue may cause various disadvantages, the concentration thereof is required to be lowered by gettering.

The surface of the crystallized semiconductor film is treated with ozone water first, and then a barrier film is formed in thickness of 1 to 5 nm on which a gettering site is formed by sputtering. The gettering site is formed by depositing an amorphous silicon film containing argon element of 50 nm in thickness. The gettering site is formed with a film forming pressure of 0.3 Pa, a flow rate of gas (Ar) of 50 (sccm), film forming power of 3 kW and substrate temperature of 150° C. Further, atomic concentration of argon element included in the amorphous silicon film falls in a range of $3\times10^{20}/cm^3$ to $6\times10^{20}/cm^3$ and atomic concentration of oxygen falls in a range of $1\times10^{19}/cm^3$ to $3\times10^{19}/cm^3$ under the above-described conditions. Thereafter, gettering is carried out by heating at 750° C. for 3 minutes by using a lamp annealing device.

After gettering, the crystalline semiconductor film is etched into semiconductor layers 102 to 105 having desired shapes. Next, a gate insulating layer 106 is formed. An insulating layer containing silicon may be formed in thickness of approximately 115 nm by low pressure CVD, plasma CVD, sputtering or the like. A silicon oxide film is formed in this embodiment. The silicon oxide film is formed by mixing TEOS (Tetraethyl Ortho Silicate) and $O_2$ by the plasma CVD with a reaction pressure of 40 Pa, the substrate temperature of 300 to 400° C., the high frequency (13.56 MHz) the power density in the range of 0.5 to 0.8 W/cm$^2$. The silicon oxide film thus prepared has an excellent characteristics as a gate insulating film after the subsequent heating at 400 to 500° C.

A tantalum nitride (TaN) film of 30 nm in thickness is formed as a first conductive layer on the gate insulating layer 106, and a tungsten (W) film of 370 nm in thickness is formed as a second conductive layer thereon. The TaN film and the W film may both be formed by sputtering. The TaN film may be formed in nitride atmosphere by using Ta as a target, and the W film may be formed by using W as a target. It is preferable in using as a gate electrode that a resistance be low, in particular the resistance of the W film be 20 μΩcm or less. Therefore, high purity (99.9999%) target of W is desirably used and further attention has to be paid not to let impurities in during deposition. The resistance of the W film formed like this can be 9 to 20μΩcm.

Note that the first conductive layer is a TaN film of 30 nm in thickness and the second conductive layer is W film of 370 nm in thickness in this embodiment, however, the first and second conductive layers may be formed of any element among Ta, W, Ti, Mo, Al, Cu, Cr, and Nd, or an alloy or a compound having the aforementioned element as a major component. Furthermore, a semiconductor film represented by a polycrystalline silicon film doped with an impurity element such as phosphorous. An alloy of AgPdCu may be utilized as well. A combination thereof may be selected in each case. The first conductive layer may have a thickness of 20 to 100 nm, the second conductive layer may have a thickness of 100 to 400 nm. In this embodiment, the lamination of two layers are employed; however, one layer or three or more layers may be laminated as well.

In order to form electrodes and wirings by etching the conductive layer, a photo resist is formed as a mask through exposure to light by photolithography. First etching is carried out under a first and second etching conditions. Etching is carried out using the mask formed of a resist to form a gate electrode and wirings. An etching condition may be determined in each case.

In the present method, ICP (Inductively Coupled Plasma) etching is used. As the first etching condition, $CF_4$, $Cl_2$, and $O_2$ are used as etching gas with the gas-flow ratio of 25/25/10 (sccm), and a pressure of 1.0 Pa and an RF power of 500 W (13.56 MHz) is applied on the coil electrode to generate plasma for etching. An RF power of 150 W (13.56 MHz) is applied to a substrate (sample stage) to apply a substantially negative self bias voltage. The W layer is etched under the first etching condition to make the edges of the first conductive layer in tapered shape. An etching rate on the W layer under the first etching condition is 200.39 nm/min, the etching rate on the TaN layer is 80.32 nm/min, and the selectivity ratio of W relatively to TaN is approximately 2.5. Further, the taper angle of the W layer is about 26° under the first etching condition.

Subsequently, etching is carried out under the second etching condition. Etching is performed for about 15 seconds with the resist as a mask remained, by using $CF_4$ and $Cl_2$ as etching gas with the gas-flow ratio of 30/30 (sccm), and a pressure of 1.0 Pa and an RF power of 500 W (13.56 MHz) is applied on the coil electrode to generate plasma for etching. An RF power of 20 W (13.56 MHz) is applied to a substrate (sample stage) to apply a substantially negative self bias voltage. Under the second etching condition in which $CF_4$ and $Cl_2$ are mixed, both of the W layer and the TaN layer are etched to the same extent.

The etching rate on the W layer under the second etching condition is 58.97 nm/min, and the etching rate on the TaN layer is 66.43 nm/min. It should be noted that in order to etch without leaving residue on the gate insulating layer, time required for etching may be increased by 10 to 20%. The gate insulating layer which is not covered with electrodes is etched by 20 to 50 nm in this first etching.

The edges of the first and second conductive layers become tapered in the first etching due to the bias voltage applied to the substrate.

The second etching is carried out without removing the resist as a mask. The etching is performed using $SF_6$, $Cl_2$, and $O_2$ as etching gas with the gas-flow ratio of 24/12/24 (sccm), and a pressure of 1.3 Pa and an RF power of 700 W (13.56 MHz) is applied on the coil electrode to generate plasma for etching for about 25 seconds. An RF power of 10 W (13.56 MHz) is applied to a substrate (sample stage) to apply a substantially negative self bias voltage. The W layer is selectively etched by this etching to form a conductive layer in a second shape. The first conductive layer is hardly etched at this time. Gate electrodes made of the first conductive layers 107a to 110a and the second conductive layers 107b to 110b are formed by the first and second etching.

A first doping is carried out without removing the resist as a mask. Thus, an N-type impurity is doped in a low concentration to a crystalline semiconductor layer. The first doping may be performed by ion doping or ion implantation. The ion doping may be performed with the dosage of $1 \times 10^{13}$ to $5 \times 10^{14}$ atoms/cm$^2$, and an acceleration voltage of 40 to 80 kV. The ion doping is carried out at an acceleration voltage of 50 kV in this embodiment. The N-type impurity may be an element of the group 15 of the periodic table represented by phosphorous (P) or arsenic (As). Phosphorous (P) is used in this embodiment. The first conductive layer is used as a mask to form a first impurity region (N region) in a self-aligned manner to which an impurity of low concentration is doped.

Subsequently, a resist as a mask is removed. Then, a new mask formed of a resist is formed and the second doping is carried out at a higher acceleration voltage than the first doping. The N-type impurity is doped in the second doping as well. The ion doping may be performed with the dosage of $1 \times 10^{13}$ to $3 \times 10^{15}$ atoms/cm$^2$, and an acceleration voltage of 60 to 120 kV. The ion doping is carried out with the dosage of $3.0 \times 10^{15}$ atoms/cm$^2$ and an acceleration voltage of 65 kV in this embodiment. The second doping is carried out so that the impurity element is doped on the semiconductor layer under the first conductive layer by using the second conductive layer as a mask against the impurity element.

By the second doping, a second impurity region (N region, Lov region) is formed on the part where the second conductive layer is not overlapped or the part which is not covered with the mask in the part where the crystalline semiconductor layer is overlapped with the first conductive layer. The N-type impurity of which concentration ranging from $1 \times 10^{18}$ to $5 \times 10^{19}$ atoms/cm$^3$ is doped on the second impurity region. Further, the exposed part (third impurity region: N$^+$ region)

which is not covered with either the first conductive layer nor the mask is doped with a high concentration N-type impurity ranging from $1\times10^{19}$ to $5\times10^{21}$ atoms/cm$^3$. The semiconductor layer has an N$^+$ region, a part of which is covered only with the mask. The concentration of the N-type impurity of this part is not changed from the impurity concentration of the first doping. Therefore, this part is referred to as the first impurity region (N region) as it is.

Note that each impurity region is formed by two doping treatments in this embodiment; however, the invention is not exclusively limited to this. The impurity region having a desired impurity concentration may be formed by one or a multiple doping by determining the condition in each case.

Subsequently, the resist as a mask is removed and a new mask formed of a resist is formed for third doping. By the third doping, a fourth impurity region (P$^+$ region) and a fifth impurity region (P region) are formed in which an impurity element having the opposite conductivity to the ones of the first and second conductive layers is added.

The fourth impurity region (P$^+$ region) is formed on the part which is not covered with the resist as a mask and not overlapped with the first conductive layer, and the fifth impurity region (P region) is formed on the part which is not covered with the resist as a mask, overlapped with the first conductive layer, and not overlapped with the second conductive layer. the P$^-$ type impurity element may be boron (B), aluminum (Al), or gallium (Ga), each of which are of the group 13 of the periodic table.

In this embodiment, boron is used as a P-type impurity element to form the fourth and fifth impurity regions by ion doping using diborane (B$_2$H$_6$). Ion doping is carried out with the dosage of $1\times10^{16}$ atoms/cm$^2$ and an acceleration voltage of 80 kV.

Note that semiconductor layers A and C for forming N-channel TFTs are covered with resists as masks in the third doping.

The fourth impurity region (P$^+$ region) and the fifth impurity region (P region) are doped with phosphorous of different concentrations by the first and second doping. However, in both of the fourth impurity region (P$^+$ region) and the fifth impurity region (P region), the third doping is performed so that the concentration of the P-type impurity element is $1\times10^{19}$ to $5\times10^{21}$ atoms/cm$^2$. Therefore, the fourth impurity region (P$^+$ region) and the fifth impurity region (P region) work as source region and drain region of a P-channel TFT without problems.

It should be noted that the fourth impurity region (P$^+$ region) and the fifth impurity region (P region) are formed by once of third doping, however, the invention is not exclusively limited to this. The fourth impurity region (P$^+$ region) and the fifth impurity region (P region) may be formed by multiple doping treatments according to each condition.

By the aforementioned doping treatments, a first impurity region (N region) 114, a second impurity region (N region, Lov region) 111, third impurity regions (N$^+$ region) 112 and 113, fourth impurity regions (P$^+$ region) 115 and 116, and fifth impurity regions (P region) 117 and 118 are formed.

Subsequently, the resist as a mask is removed to form a first passivation layer 119. As a first passivation layer, an insulating film containing silicon is formed in thickness of 100 to 200 nm by plasma CVD or sputtering. In this embodiment, a silicon oxynitride film is formed in thickness of 100 nm by plasma CVD. In the case of using a silicon oxynitride film, a silicon oxynitride film formed of SiH$_4$, N$_2$O, and NH$_3$ by plasma CVD, or a silicon oxynitride silicon film formed of SiH$_4$ and N$_2$O may be used. In this case, the film is formed with a reaction pressure of 20 to 200 Pa, a substrate temperature of 300 to 400° C., and a high frequency (60 MHz) electronic density 0.1 to 1.0 W/cm$^2$. Further, a silicon oxynitride hydride film formed of SiH$_4$, N$_2$O, and H$_2$ may be employed as the first passivation layer. It is needless to say that the first passivation layer 119 is not limited to a single layer structure of the silicon oxynitride film as in this embodiment, but other insulating layer containing silicon may be utilized in a single or a laminated structure.

Thereafter, crystallinity of the semiconductor layer is recovered and the impurity element doped in the semiconductor layer is activated by heating. Heating may be performed under the conditions of oxygen concentration of 1 ppm or less, preferably in the nitrogen atmosphere of 0.1 ppm or less, at a temperature of 400 to 700° C. In this embodiment, the semiconductor layer is activated by heating at a temperature of 410° C. for one hour. Note that laser annealing or rapid thermal annealing (RTA) may be employed instead of heating.

By heating the semiconductor layer after forming the first passivation layer 119, it can be hydrogenated as well as activated. By hydrogenation, a dangling bond in the semiconductor layer is terminated by hydrogen in the first passivation layer.

Heat treatment may be carried out before forming the first passivation layer 119; however, it is preferable to carry out the heat treatment after forming the first passivation layer 119 in order to protect wirings and the like in the case where the materials constituting first conductive layers 107a to 110a and second conductive layers 107b to 110b are sensitive to heat. Further, in the case of heating before forming the first passivation layer, hydrogenation by using hydrogen contained in the passivation layer cannot be performed as the first passivation layer is not formed yet.

In this case, hydrogenation by using hydrogen excited by plasma (plasma hydrogenation) or by heating at a temperature of 300 to 450° C. for 1 to 12 hours in an atmosphere containing 3 to 100% of hydrogen.

Subsequently, a first interlayer insulating layer 120 is formed on the first passivation layer 119. The first interlayer insulating layer may be an inorganic insulating layer or an organic insulating layer. The inorganic insulating layer may be a silicon oxide film formed by CVD, a silicon oxide film applied by SOG (Spin On Glass), and the organic insulating layer may be a film of polyimide, polyamide, BCB (benzocyclobutene), acryl or positive photosensitive organic resin, negative photosensitive organic resin and the like. Also, a lamination of the acryl film and the silicon oxynitride film may be used.

A non-photosensitive acryl film is formed in thickness of 1.6 μm in this embodiment. By use of the first interlayer insulating layer, projective and recessed portions of the TFTs formed on the substrate can be alleviated and the substrate can be planarized. The first insulating layer plays a significant role in planarization, therefore, an easily planarized material is preferably used.

Thereafter, a second passivation layer (not shown) formed of a silicon nitride oxide film and the like is formed on the first interlayer insulating layer. The second passivation layer may be formed in thickness of 10 to 200 nm approximately, which can protect the first interlayer insulating layer from moisture. The second passivation layer may be a silicon nitride film, an aluminum nitride film, an aluminum oxynitride film, a diamond-like carbon (DLC), and a carbon nitride (CN) film.

A film formed by RF sputtering has an excellent density and barrier performance. In the case of forming a silicon oxynitride film for example, RF sputtering is performed with Si as a target and N$_2$, Ar, N$_2$O with the gas-flow ratio of 31:5:4, a pressure of 0.4 Pa, and power of 3000 W. In the case of forming a silicon nitride oxide film, RF sputtering is performed with Si as a target and $N_2$ and Ar in the chamber with the gas-flow ratio of 20:20, a pressure of 0.8 Pa, and power of 3000 W at a temperature of 215° C. In this embodiment, a silicon oxynitride film is formed in thickness of 70 nm by RF sputtering.

The second passivation layer, the first interlayer insulating layer and the first passivation layer are etched to form contact holes to reach the third and fourth impurity regions.

Subsequently, wirings and electrodes 122 to 129 are formed each of which connects to each impurity region electrically. It should be noted that these wirings are formed by patterning the lamination of Ti film of 50 nm in thickness and an alloy film (Al and Ti) of 500 nm in thickness. It is needless to say that the lamination is not limited to two-layer lamination, but a signal layer or three or more layers may be laminated as well. Further, material for the wirings is not limited to Al and Ti. For example, a lamination in which an Al film or a Cu film may be formed on the TaN film and then Ti film is formed thereon may be patterned to form wirings.

A TFT formed by the method for testing of the invention has less defects and provides a good and uniform quality, therefore it can be applied to a variety of electronic devices and display devices in particular. Thus, the reliability of the products can be improved as well.

Embodiment 2

In the present embodiment, an example in which the TFT fabricated according to the invention is used for manufacturing a display device is described.

A first electrode 150 formed of a transparent conductive film is formed so as to partially overlap with the wiring 127 of a TFT. The transparent conductive film is preferably formed by using a material with a high work function, for example, a compound of indium oxide and tin oxide (ITO), a compound of indium oxide and zinc oxide, zinc oxide, tin oxide, indium oxide or titanium nitride can be used. Alternatively, the transparent conductive film added with gallium may be used. The first electrode 150 serves as an anode of the light emitting element. In this embodiment, ITO is used as the first electrode 150. The ITO is formed in thickness of 0.1 µm by sputtering.

Figure 18A:
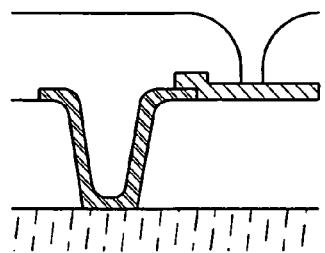
FIGS. 18A-18F are diagrams showing an embodiment of the invention.
Figure 18B:
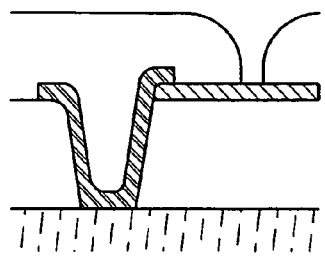
Figure 18C:
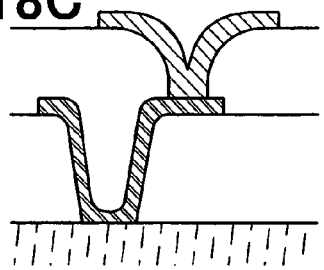
Figure 18D:

The transparent conductive film is formed after forming the wiring 127 of the TFT in this embodiment, however, it may be formed before forming the wiring 127 as shown in FIG. 18B or it may be formed by opening a contact hole after forming the wiring 127 and an insulator in this order (FIG. 18C). FIG. 18A shows the method of the present embodiment.

Figure 18E:
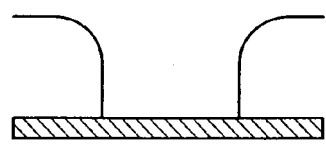
Figure 18F:
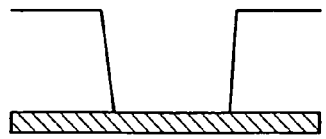

Subsequently, an insulator 151 is formed so as to cover the end surface of the electrode. The insulator 151 can be formed by an inorganic or organic material. It is advantageous to form by using a photosensitive organic material since disconnection between the steps and the like do not occur easily in the aperture when depositing a light emitting layer. In the case of using a negative photosensitive acryl for the insulator 151, the insulator 151 can be formed such that the top portion thereof comprises a curved face having a first radius of curvature and the bottom portion thereof comprises a curved face having a second radius of curvature. The first and second radiuses of curvature are preferably 0.2 to 3 µm and the angle respectively to the ITO on the wall of the aperture is preferably 35° or more. Further, the photosensitivity is not limited to negative, but positive type can also be used. In the case of using the positive photosensitivity, the top portion of the insulator 151 comprises a curved face having the second radius of curvature as shown in FIG. 18E. When fabricating the aperture of the insulator 151 by dry etching instead of using a photosensitive organic material, the insulator 151 has the aperture having a shape as shown in FIG. 18F.

Thereafter, the substrate is removed of dusts and the like by wiping with a PVA (polyvinyl alcohol)-based porous material. It should be noted that in this embodiment, fine powder (dusts) generated when the ITO and the insulating layer are etched are removed by wiping with the PVA-based porous material.

Subsequently, PEDOT may be applied on the whole surface and baked before depositing a light emitting layer. At this time, it is preferable to rinse the substrate after applying PEDOT, and then apply PEDOT again. Then, the substrate is heated in a low pressure atmosphere after vaporizing moisture by heating at normal pressure. It should be noted that the substrate is heated at 170° C. at a low pressure atmosphere for four hours after applying PEDOT, and then allowed to be cooled for 30 minutes.

Then, the substrate is deposited by moving an evaporation source with a deposition device. For example, deposition is performed in a deposition chamber which is vacuum evacuated to $5 \times 10^3$ Torr (0.665 Pa) or less, more preferably to $10^4$ to $10^6$ Torr. When deposition is performed, an organic compound is vaporized by resistive heating in advance and flies in the direction of the substrate when a shutter is opened in deposition. The vaporized organic compound flies upward and is deposited to the substrate through the aperture provided on a metal mask to form a light emitting layer 152 (including a hole transport layer, a hole injection layer, an electron transport layer, and an electron injection layer).

Shown here is an example in which the light emitting layer 152 is formed by deposition, however, the invention is not exclusively limited to this. A light emitting layer formed of high-molecular material may be formed by coating (such as spin coating or inkjet). Further, the present embodiment describes an example in which layers formed of low-molecular material are laminated as an organic compound layer, however, a layer formed of high-molecular material and a layer formed of low-molecular material may be laminated as well. In addition, RGB light emitting layers may be formed to achieve full color display, or in the case of forming a monochrome light emitting layer, full color display may be achieved by using a color conversion layer or a color filter. Inorganic material may be used as well.

It is assumed that a light emitting element emits light in such a way that an electron injected from cathode and a hole injected from anode form a molecular exciton by recombining at the center of light emission in the organic compound layer when a voltage is applied to an organic compound layer sandwiched between a pair of electrodes, and energy for light emission generates when the molecular exciton turns back to the normal state. The exciton state is known to include a singlet exciton and a triplet exciton, through either of which light can be emitted.

A light emitting layer typically has a laminated structure. The typical laminated structure is constituted as "a hole transport layer, an electroluminescent layer, and an electron transport layer,". This structure has such a high luminous efficiency that the light emitting devices which are recently researched and developed mostly employ this structure. The structure in which a hole injection layer, a hole transport layer, an electroluminescent layer, and an electron transport layer are laminated on the anode, or a structure in which a hole injection layer, a hole transport layer, an electroluminescence layer, an electron transport layer, and an electron injection layer are laminated in these orders may be employed as well. A fluorescent pigment and the like may be doped on the electroluminescent layer.

It should be noted that all the layers provided between the cathode and anode are referred to as a light emitting layer collectively. Therefore, the aforementioned hole injection layer, hole transport layer, electroluminescent layer, electron transport layer and electron injection layer are all included in the light emitting layer. These layers can be formed of any one or a combination of a low-molecular organic compound material, a medium-molecular organic compound material, or high-molecular organic compound material appropriately. In addition, a mixed layer of an electron transport material and a hole transport material, or a mixed junction in which a mixed region is formed in each junction boundary may be formed. An inorganic light emitting material may be used instead of the organic material.

Subsequently, a second electrode 153 is formed as a cathode on the light emitting layer. The second electrode 153 may be formed of a thin film containing a metal with a low work function (Li, Mg, or Cs). In addition, it is preferable that the second electrode be made of a laminated film in which a transparent conductive film (ITO (alloy of indium oxide and tin oxide), alloy of indium oxide and zinc oxide ($In_2O_3$—ZnO), zinc oxide (ZnO), or the like) be laminated on the thin film containing Li, Mg, Cs, or the like. Further, the second electrode may be formed in thickness of 0.01 to 1 µm by electron beam deposition, although the film thickness may be determined appropriately to serve as a cathode.

In the case of using the electron beam deposition, radioactive rays are generated when the acceleration voltage is too high, which damage a TFT. On the other hand, in the case where the acceleration voltage is too low, a deposition rate is lowered and the productivity is decreased. In view of the foregoing problems, the second electrode 153 is not formed thicker than the thickness to serve as a cathode. When the cathode is thin, the productivity is not affected much even when the deposition rate is low. Although resistance may become higher due to the thin cathode in this case, this problem can be solved by laminating a low resistance metal such as Al on the cathode by resistive heating, sputtering and the like.

On the insulator 151 and the second electrode 153, a third passivation layer 154 is formed. The second passivation layer and the third passivation layer 154 are both formed of a material which hardly penetrate the substance such as moisture and oxygen which deteriorate a light emitting element. It is preferable to use typically a DLC film, a carbon nitride film, a silicon nitride film formed by RF sputtering and the like. The film thickness is preferably 10 to 200 nm approximately.

Thus, a light emitting element as shown in FIG. 17B can be obtained. A plastic film is provided as a sealing member thereon and inert gas is filled between the light emitting element and the sealing member, which will be described with reference to FIGS. 20A to 20C. Then, the substrate is connected to an external terminal by an FPC (Flexible Printed Circuit) by using anisotropic conductive film to complete a light emitting display device (display module).

Figure 19:
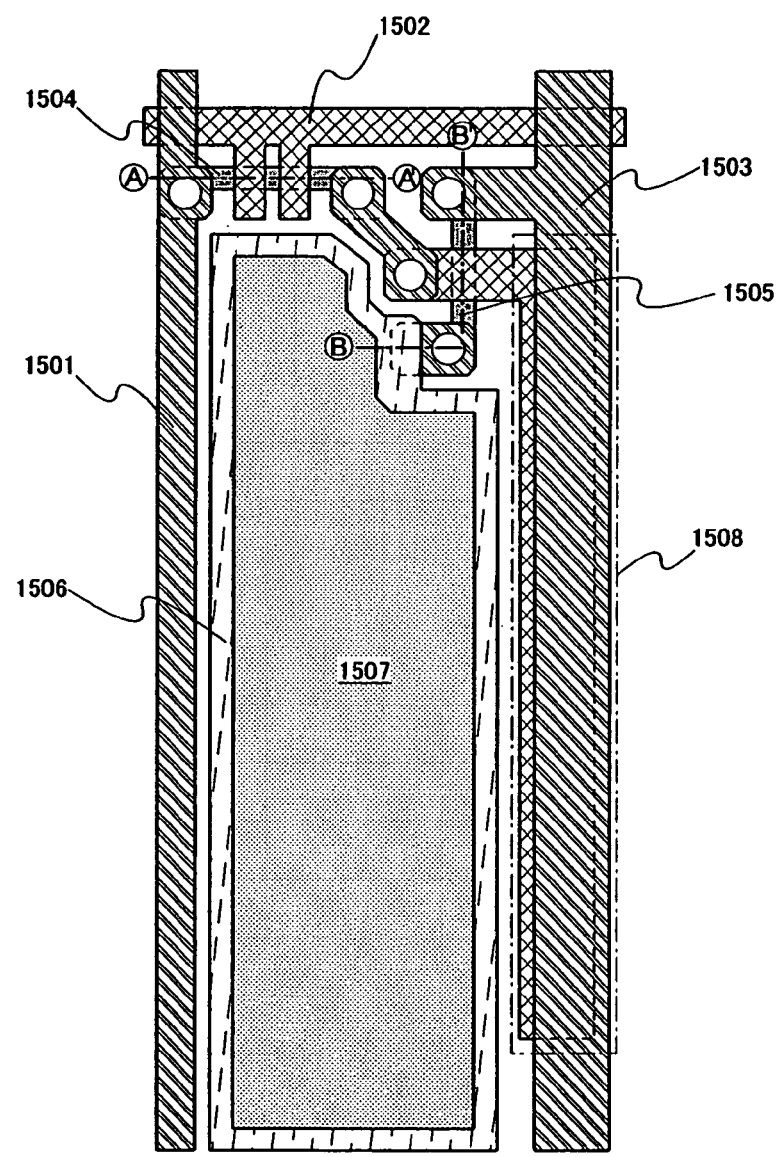
FIG. 19 is a diagram showing an embodiment of the invention.

FIG. 19 shows a top plan view of a pixel portion of the light emitting display device. A line A-A' and a line B-B' in FIG. 19 correspond to a line A-A' and a line B-B' in FIG. 17B respectively.

The pixel portion includes a source signal line 1501, a gate signal line 1502, a current supply line 1503, a switching TFT 1504, a driving TFT 1505, a pixel electrode 1506, a light emitting element 1507, and a storage capacitor 1508.

In this embodiment, light is emitted from the substrate side (bottom). Light can also be emitted from the top with a laminated structure shown in FIG. 17B. In that case, the second electrode may be formed of a translucent material.

According to the invention, a high speed operation can be realized because the gate insulating film of TFT is thin, thus a display device having an excellent display performance can be provided.

Embodiment 3

Figure 20A:
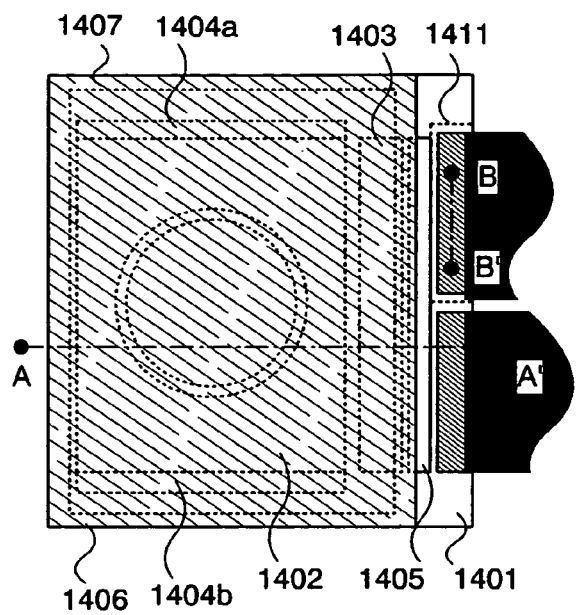
FIGS. 20A to 20C are diagrams showing an embodiment of the invention.
Figure 20B:
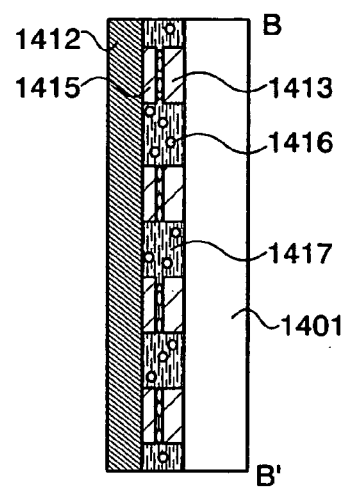

The overall structure of the semiconductor device is described with reference to FIGS. 20A to 20C. FIG. 20A shows a top plan view of the semiconductor device formed by sealing a substrate on which TFTs are formed with a sealing member. FIG. 20B shows a sectional view cut along the line B-B' in FIG. 20A, and FIG. 20C shows a sectional view cut along the line A-A' in FIG. 20A.

Figure 20C:
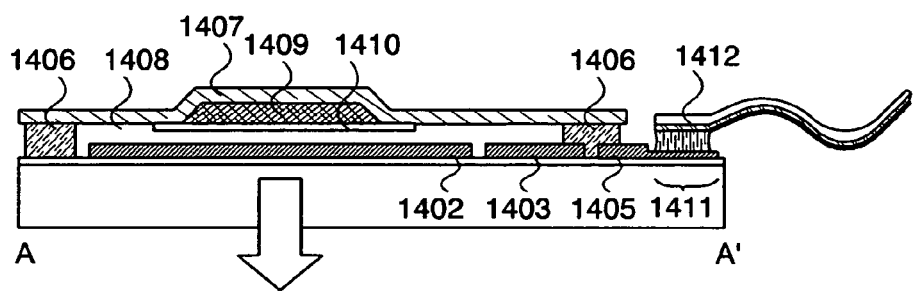

In FIGS. 20A to 20C, a substrate 1401 has a pixel portion (display portion) 1402, a signal driver circuit 1403 provided so as to surround the pixel portion 1402, scanning driver circuits 1404a and 1404b, a protection element 1405, and a sealing member 1406 so as to surround the aforementioned portions. The pixel portion 1402 may be configured as described above in the embodiments. As for the sealing member 1406, glass, metal (representatively, stainless material), ceramics, or plastic (including plastic film) is used.

The sealing member 1406 may be provided over parts of the signal driver circuit 1403, the scanning driver circuits 1404a and 1404b, and the protection element 1405. A sealing member 1407 is provided on the sealing member 1406, and thus a sealed space 1408 is formed by the substrate 1401, the sealing members 1406 and 1407. The sealing member 1407 is provided with a moisture-absorbing agent 1409 (barium oxide, calcium oxide or the like) in its recessed portion, which maintains the atmosphere of the sealed space 1408 clean by absorbing moisture, oxygen and the like and suppress the deterioration of the light emitting element. The recessed portion is covered with a fine mesh cover member 1410 which passes through air and moisture but not the moisture-absorbing agent 1409. The sealed space 1408 may be filled with noble gas such as nitrogen and argon, otherwise resin or liquid as long as it is inert.

An input terminal 1411 is provided on the substrate 1401 for transmitting signals to the signal driver circuit 1403 and the scanning driver circuits 1404a and 1404b. Data signals such as video signals are transmitted to the input terminal 1411 through an FPC 1412. A cross section of the input terminal 1411 is shown in FIG. 20B in which an input wiring 1413 formed at the same time with the scanning or signal lines, and a wiring 1415 provided on the FPC 1412 side are connected electrically by using a resin 1417 in which a conductor 1416 is scattered. It should be noted that the conductor 1416 may be a spherical high-molecular compound plated with gold or silver.

In this embodiment, the protection element 1405 is provided between the pixel portion 1402 and the signal driver circuit 1403, and the input terminal 1411. The protection element 1405 provided between the input terminal 1411 and the signal driver circuit 1403 releases a pulse signal to the outside when electrostatic such as pulse signal is inputted suddenly between the input terminal 1411 and the signal driver circuit 1403. It is needless to say that the protection element 1405 may be provided in other part such as between the pixel portion 1402 and the signal driver circuit 1403, or between the pixel portion 1402 and the scanning driver circuits 1404*a* and 1404*b*.

Embodiment 4

Examples of the electric device employing the invention include a video camera, a digital camera, a goggle type display (head mounted display), a navigation system, an audio reproducing device (such as car audio system and audio component system), a notebook computer, a game machine, a portable information terminal (such as mobile computer, mobile telephone, portable game machine, and electronic book), and an image reproducing device provided with a recording medium (specifically, a device adapted to reproduce a recording medium such as a digital versatile disc (DVD) and provided with a display device capable of displaying an image thereof). FIGS. 21A to 21H show specific examples thereof.

Figure 21A:
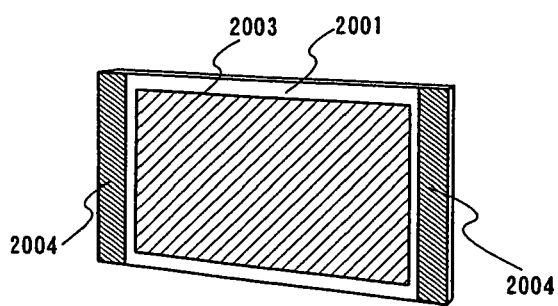
FIGS. 21A to 21H are diagrams showing an embodiment of the invention.

FIG. 21A shows a light emitting display device such as a TV receiver, including a housing 2001, a display portion 2003 and a speaker portion 2004. The invention can be applied to the display portion 2003. A polarizer or a circular polarizer may be provided in the pixel portion in order to improve the contrast. For example, a ¼ ë plate, a ½ ë plate, and a polarizer may be provided in this order in the sealing substrate. Further, an antireflection film may be provided on the polarizer.

Figure 21B:
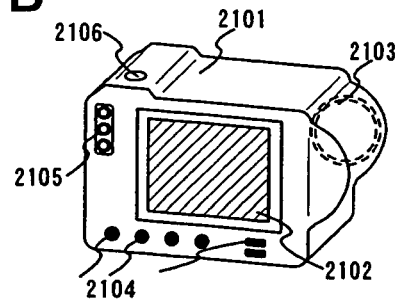

FIG. 21B shows a digital still camera including a main body 2101, a display portion 2102, an image receiving portion 2103, operation keys 2104, an external connection port 2105, a shutter 2106, etc. The invention can be applied to the display portion 2102.

Figure 21C:
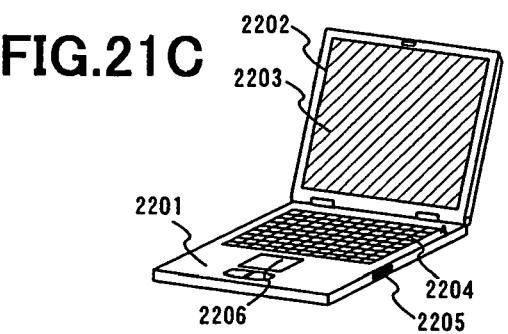

FIG. 21C shows a notebook computer, including a main body 2201, a housing 2202, a display portion 2203, a keyboard 2204, an external connection port 2205, a pointing mouse 2206, etc. The present invention can be applied to the display portion 2203.

Figure 21D:
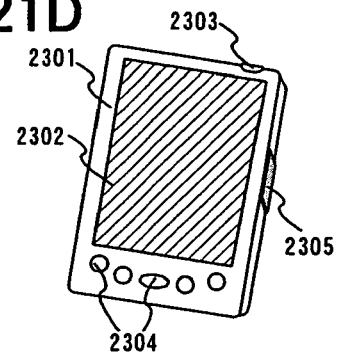

FIG. 21D shows a mobile computer including a main body 2301, a display portion 2302, a switch 2303, operation keys 2304, an infrared port 2305, etc. The invention can be applied to the display portion 2302.

Figure 21E:
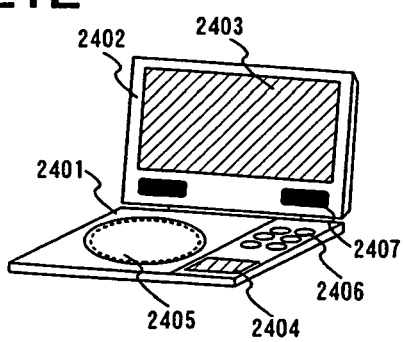

FIG. 21E shows a portable image reproducing device having a recording medium (a DVD player, to be specific). The device includes a main body 2401, a housing 2402, a display portion A 2403, a display portion B 2404, a recording medium (DVD or the like) reading unit 2405, an operation key 2406, a speaker unit 2407, etc. The display portion A 2403 mainly displays image information whereas the display portion B 2404 mainly displays text information. The invention can be applied to both the display portions A 2403 and B 2404. Domestic video games and the like are also included in the image reproducing device having a recording medium.

Figure 21F:
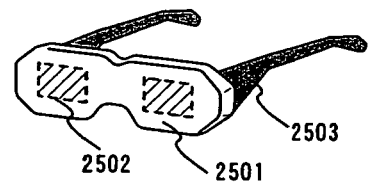

FIG. 21F shows a goggle type display (head mounted display), including a main body 2501, a display portion 2502, and an arm portion 2503. The invention can be applied to the display portion 2502.

Figure 21G:
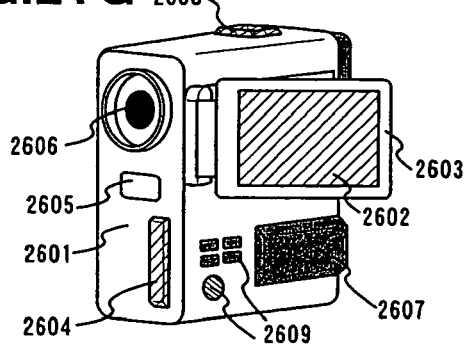

FIG. 21G shows a video camera including a main body 2601, a display portion 2602, a housing 2603, an external connection port 2604, a remote control receiving portion 2605, an image receiving portion 2606, a battery 2607, an audio input portion 2608, operation keys 2609, etc. The invention can be applied to the display portion 2602.

Figure 21H:
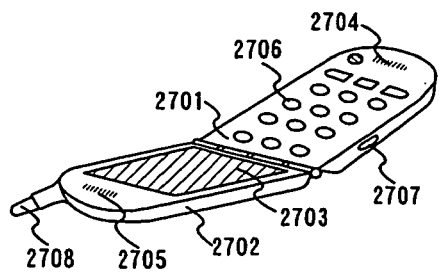

FIG. 21H shows a mobile phone including a main body 2701, a housing 2702, a display portion 2703, an audio input portion 2704, an audio output portion 2705, an operation key 2706, an external connection port 2707, an antenna 2708, etc. The present invention can be applied to the display portion 2703. In the case where the display portion 2703 displays white letters on black background, the mobile phone consumes less power.

It should be noted that when a higher luminance of a light emitting material is realized in the future, a light including the outputted image data will be able to be used in a front or rear projector by expanding and projecting the image by using a lens and the like.

The aforementioned electronic devices are more likely to be used for displaying information distributed through a telecommunication path such as Internet, a CATV (Cable Television System), and in particular moving picture information is likely to be displayed. The light emitting device is suitable for displaying moving pictures since the light emitting material can exhibit a remarkably high response.

As set forth above, the present invention can be applied to a wide range of electronic devices in all fields. Furthermore, crystallization by using a laser irradiation device which costs high for operation can be carried out more efficiently, thus the defects are decreased and the low price can be realized as well. Moreover, reliability of the products can be improved, which leads to the improvement of the reliability of a manufacturer.

Embodiment 5

Each of the electronic devices described in Embodiment 4 includes a module in which the panel sealing light emitting element or liquid crystal element is provided with a controller and an IC including a power supply circuit and the like. The module and the panel both correspond to one mode of the light emitting device. In this embodiment, a specific configuration of the module will be described.

Figure 22A:
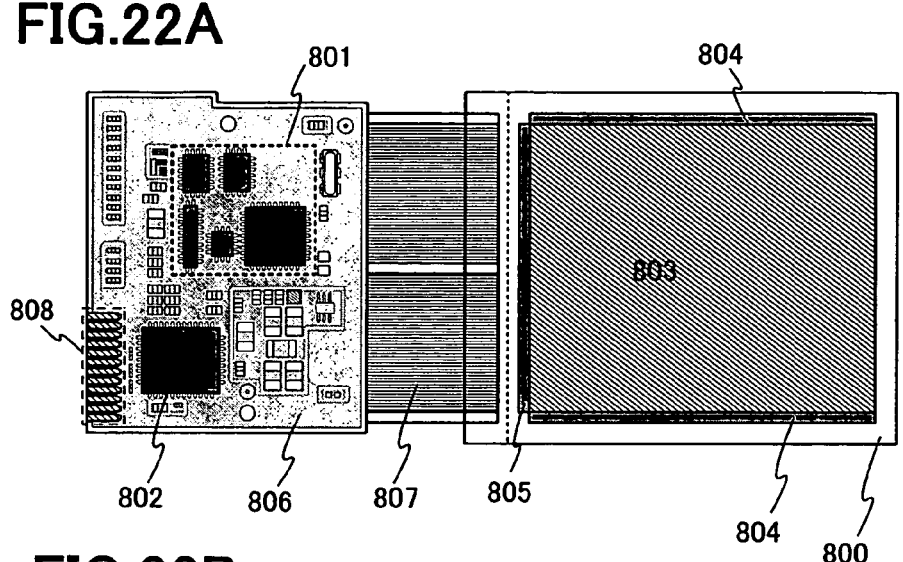
FIGS. 22A and 22B are diagrams showing an embodiment of the invention.

FIG. 22A shows an appearance of a module in which a panel 800 is provided with a controller 801 and a power supply circuit 802. The panel 800 comprises a pixel portion 803 in which a light emitting element is provided in each pixel, a scanning driver circuit 804 for selecting a pixel in the pixel portion 803, and a signal driver circuit 805 for supplying a video signal to the selected pixel.

A controller 801 and the power supply circuit 802 are provided on a printed substrate 806, various kinds of signals and power supply voltage outputted from the controller 801 or the power supply circuit 802 are supplied via an FPC 807 to the pixel portion 803, the scanning driver circuit 804, and the signal driver circuit 805 of the panel 800.

The power supply voltage and various kind of signals are supplied to the printed substrate 806 via an interface (I/F) 808 in which a plurality of input terminals are arranged.

It should be noted that the printed substrate 806 is mounted on the panel 800 with the FPC 807 in this embodiment, however the invention is not limited to this configuration. The controller 801 and the power supply circuit 802 may be provided directly on the panel 800 by COG (Chip On Glass) method.

Further, in the printed substrate 806, noise may be generated to the power supply voltage or signals, or the rise of the signal may become slow due to a capacitance formed between drawn wirings, resistance of the wiring itself and the like. Therefore, elements such as a capacitor and a buffer may be provided on the printed substrate 806, thereby preventing the noise from generating to the power supply voltage or signals, or preventing the rise of the signal from becoming slow.

Figure 22B:
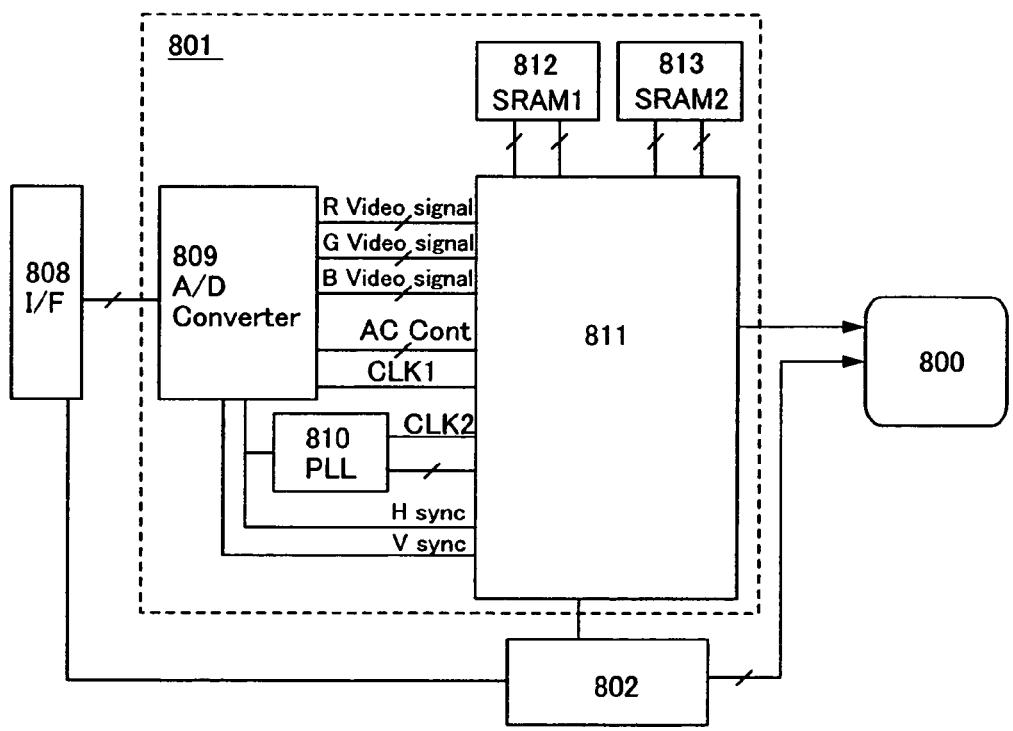
Figure 23A:
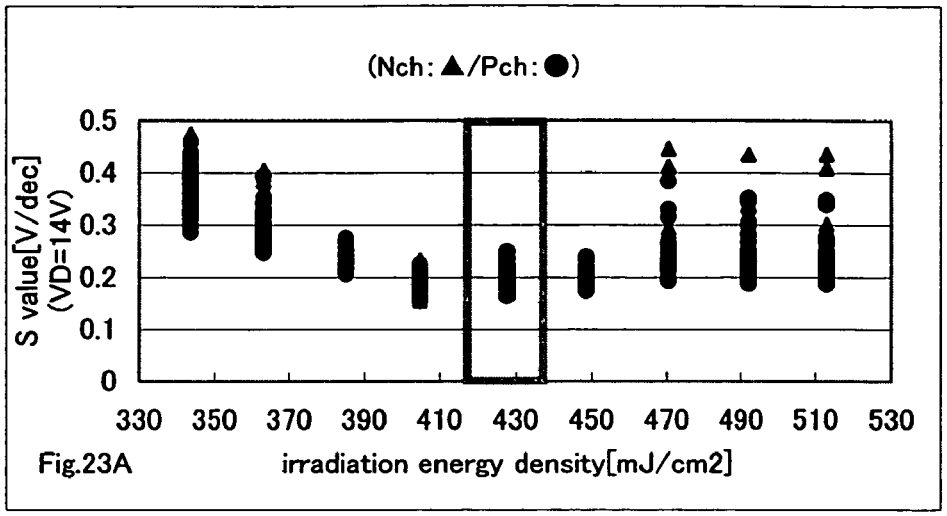
FIGS. 23A-23C are diagrams showing a crystallization energy and TFT characteristics.
Figure 23B:
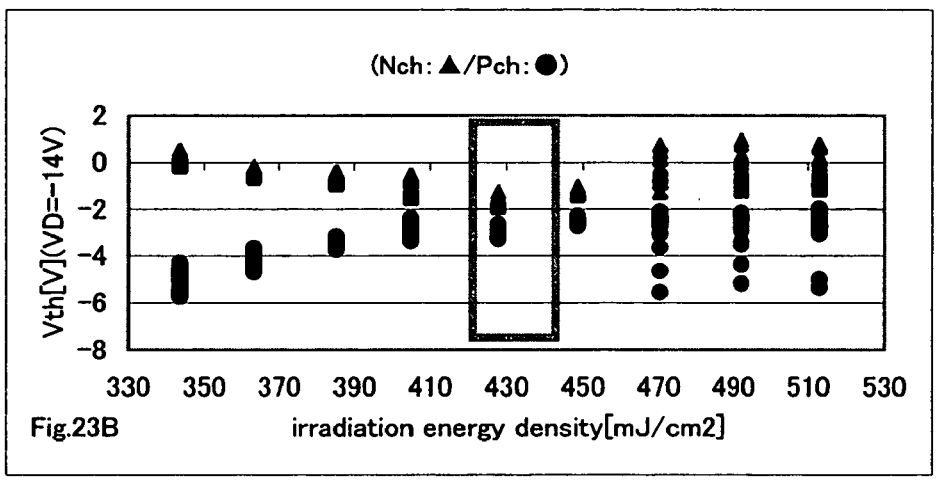
Figure 23C:
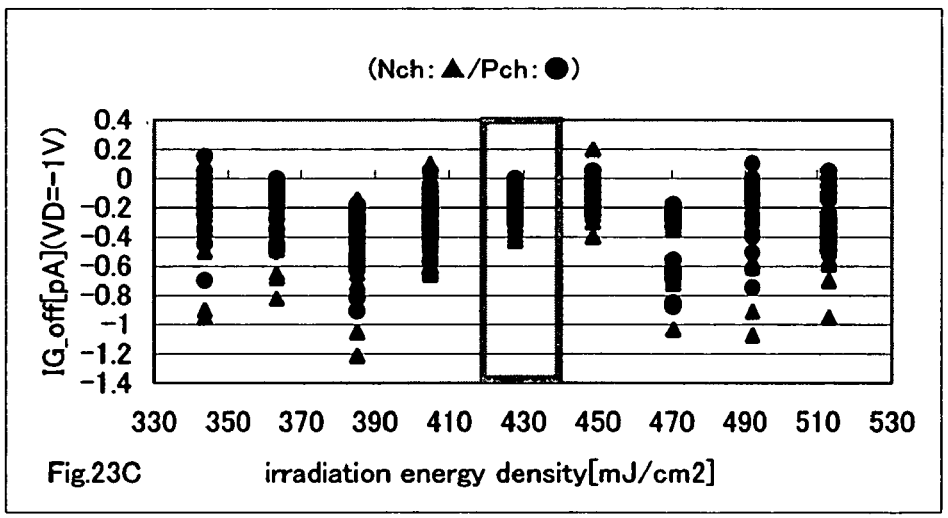

FIG. 22B is a block diagram of a configuration of the printed substrate 806. The signals and the power supply voltage supplied to the interface 808 are supplied to the controller 801 and the power supply circuit 802.

The controller 801 includes a phase locked loop (PLL) 810, a control signal generating portion 811, and an A/D converter 809 and SRAMs (Static Random Access Memories) 812 and 813 as appropriate, such as the case where the inputted signal is an analog signal or a digital signal, or the case where pixels of a panel is controlled by either of analog signals or digital signals. Note that, an SDRAM may also be used instead of the SRAM, or a DRAM (Dynamic Random Access Memory) may also be used as long as writing and reading of data can be performed at a high rate.

The video signals supplied through the interface 808 are subjected to parallel-serial conversion in the A/D converter 809, and the resultant signals, which serve as the video signals corresponding to the respective colors of R, G, and B, are inputted to a control signal generating portion 811. Further, an Hsync signal, a Vsync signal, a clock signal CLK, and an alternating voltage (AC Cont) are generated in the A/D converter 809 based on the respective signals supplied through the interface 808, and are inputted to the control signal generating portion 811.

The phase locked loop 810 controls a phase of a frequency of each of the signals supplied through the interface 808 and a phase of an operation frequency of the control signal generating portion 811. The operation frequency of the control signal generating portion 811 is not necessarily the same as the frequency of each of the signals supplied through the interface 808. Thus, the operation frequency of the control signal generating portion 811 is regulated in the phase locked loop 810 for synchronization of the above phases.

Note that when a video signal is inputted to the control signal generating portion 811, it is once written to and held in the SRAMs 812 and 813. In the control signal generating portion 811, the video signals corresponding to all the pixels are read out among the video signals of all the bits held in the SRAM 812 on a bit-by-bit basis, and are supplied to the signal line driver circuit 805 of the panel 800.

Further, information of each bit on a period during which a light emitting element emits light is supplied from the control signal generating portion 811 to the scanning driver circuit 804 of the panel 800.

Further, a predetermined power supply voltage is supplied from the power supply circuit 802 to the signal driver circuit 805, the scanning driver circuit 804, and the pixel portion 803 of the panel 800.

Embodiment 6

In this embodiment, an example where the beam profile of the energy beam is tested according to the invention is described with reference to FIGS. 24A and 24B.

One of the important factors in irradiating energy beam uniformly is the energy distribution profile (beam profile) of a beam spot on the irradiated part. The beam profile is sensed and controlled by using a card type UV sensor and a beam profiler (a laser beam is directly measured by CCD).

However, in the case of using the beam profiler, an actual crystallization state and the energy distribution profile measured by the beam profiler do not match. This is considered to be because a threshold of crystallization and the threshold sensed by the CCD differ, and further the temperature gradient at the edge of the beam spot affects the crystallization in the case of crystallizing by actually irradiating energy beam onto the object.

On the other hand, it is difficult to obtain an accurate beam profile by using the card type UV sensor due to low precision.

In this embodiment, the irradiated object on a substrate is actually irradiated by one pulse of energy beam and be crystallized by one pulse. The substrate is photographed in a dark field and processed as "an image processing commonly performed" as described in Embodiment Mode 1, thus the beam profile is tested. In this case, the irradiated object is sectioned into basic units as in Embodiment Mode 1. In the case of testing the beam profile, it is defined that the major axis of the beam spot is an X direction and the minor direction thereof is a Y axis direction.

Figure 24A:
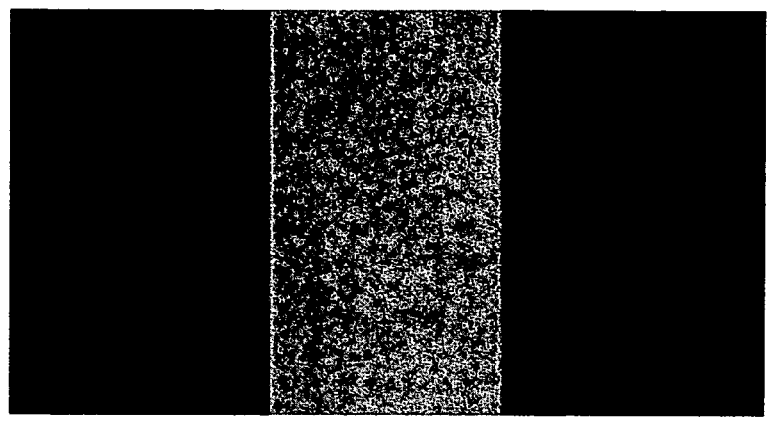
FIGS. 24A and 24B are images showing a beam profile testing.

FIG. 24A shows an analysis region extracted according to this embodiment. In this image, the black parts are not irradiated by laser, while a bright and blue part is irradiated by laser by one pulse.

After sectioning the analysis region, an average ($Bav_{Y_m}$) or a sum ($Bt_{Y_m}$) of the luminance of basic units having the same Y coordinate in the analysis region are obtained. When obtained $Bav_{Y_m}$ or $Bt_{Y_m}$ is plotted against the corresponding Y coordinate, the most adequate beam profile can be obtained. A desired beam profile can be obtained by controlling optical system according to this.

Note that an average or a sum of the luminance used in this embodiment can be replaced with an average or a sum of the corrected saturation for performing the same test.

Figure 24B:
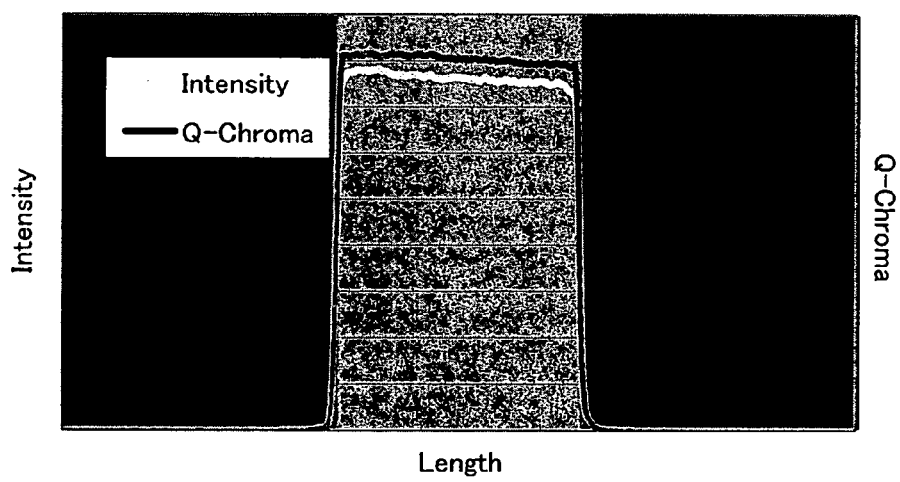

FIG. 24B is an image of the graph having the sum of the luminance and the corrected saturation of the basic units of the same Y coordinate as a vertical axis and the corresponding Y coordinate as a horizontal axis, on which an image of the analysis region is superposed by aligning the Y directions. A profile of the beam spot can be obtained in this manner.

The beam profile obtained like this reflects a temperature gradient in the edge of the beam spot when crystallized, therefore, it is very favorable and advantageous in setting the crystallization condition.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for testing comprising:
    producing a digital image by taking a visible light dark field photograph of a semiconductor film, the semiconductor film having a crystallinity that has been improved by irradiating an energy beam,
    wherein a direction in which the energy beam has been scanned is a Y direction, and a direction perpendicular to the Y direction is an X direction in the digital image;
    defining a plurality of m×n basic units by dividing the digital image into n columns in the X direction and m rows in the Y direction in a predetermined analysis range in the digital image;
    calculating an average value of corrected saturations of n basic units of the digital image aligned in the X direction for each of the m rows aligned in the Y direction;
    obtaining an approximate line, one coordinate of a point of the approximate line being a position in the Y direction, and another coordinate of the point being the calculated average value of corrected saturations in the X direction for the position in the Y direction; and
    comparing a fluctuation obtained from relations between the approximate line and the average values of corrected saturations with a reference value which is determined for a demanded performance of a semiconductor element that would comprise the semiconductor film, in order to evaluate the crystallinity of the semiconductor film having the crystallinity that has been improved.

2. The method for testing according to claim 1, wherein the energy beam is a laser light.

3. The method for testing according to claim 1, wherein the visible light used for taking the dark field photograph of the semiconductor film is irradiated from a light source selected from the group consisting of a metal halide lamp, a halogen lamp, a tungsten lamp, a xenon lamp, a light emitting diode, and a fluorescent lamp.

4. The method for testing according to claim 1, wherein an illumination intensity of the visible light used for taking the dark field photograph of the semiconductor film is 10,000 lux or more.

5. The method for testing according to claim 4, wherein the illumination intensity is from 20,000 to 100,000 lux.

6. A manufacturing method of a semiconductor device, comprising:
    testing each of a plurality of semiconductor films crystallized by the energy beam set to different energy densities by the method for testing according to claim 1; and
    determining an irradiation energy density by a result of the testing to crystallize the semiconductor film.

7. The manufacturing method according to claim 6, wherein a means for taking the visible light dark field photograph of the semiconductor film is provided in a crystallization chamber.

8. The method for testing according to claim 1, wherein the visible light used for taking the dark field photograph of the semiconductor film is of an arbitrary wavelength provided it is visible.

9. The method for testing according to claim 1, wherein the visible light used for taking the dark field photograph of the semiconductor film is emitted by a ring light.

10. The method for testing according to claim 1, wherein the dark field photograph of the semiconductor film is taken in a single shot.

11. A method for testing comprising:
    producing a digital image by taking a visible light dark field photograph of a semiconductor film, the semiconductor film having a crystallinity that has been improved by irradiating an energy beam,
    wherein a direction in which the energy beam has been scanned is a Y direction, and a direction perpendicular to the Y direction is an X direction in the digital image;
    defining a plurality of m×n basic units by dividing the digital image into n columns in the X direction and m rows in the Y direction in a predetermined analysis range in the digital image;
    calculating an average value of luminances of n basic units aligned in the X direction for each of the m rows aligned in the Y direction;
    obtaining an approximate line, one coordinate of a point of the approximate line being a position in the Y direction, and another coordinate of the point being the calculated average value of luminances in the X direction for the position in the Y direction; and
    comparing a fluctuation obtained from relations between the approximate line and the average values of luminances with a reference value which is determined for a demanded performance of a semiconductor element that would comprise the semiconductor film, in order to evaluate the crystallinity of the semiconductor film having the crystallinity that has been improved.

12. The method for testing according to claim 11, wherein the crystallinity of the semiconductor film is tested by further using an average corrected saturation in the digital image.

13. The method for testing according to claim 11, wherein the energy beam is a laser light.

14. The method for testing according to claim 11, wherein the visible light used for taking the dark field photograph of the semiconductor film is irradiated from a light source selected from the group consisting of a metal halide lamp, a halogen lamp, a tungsten lamp, a xenon lamp, a light emitting diode, and a fluorescent lamp.

15. The method for testing according to claim 11, wherein an illumination intensity of the visible light used for taking the dark field photograph of the semiconductor film is 10,000 lux or more.

16. The method for testing according to claim 15, wherein the illumination intensity is from 20,000 to 100,000 lux.

17. A manufacturing method of a semiconductor device, comprising:
    testing each of a plurality of semiconductor films crystallized by the energy beam set to different energy densities by the method for testing according to claim 11; and
    determining an irradiation energy density by a result of the testing to crystallize the semiconductor film.

18. The manufacturing method according to claim 17, wherein a means for taking the visible light dark field photograph of the semiconductor film is provided in a crystallization chamber.

19. The method for testing according to claim 11, wherein the visible light used for taking the dark field photograph of the semiconductor film is of an arbitrary wavelength provided it is visible.

20. The method for testing according to claim 11, wherein the visible light used for taking the dark field photograph of the semiconductor film is emitted by a ring light.

21. The method for testing according to claim 11, wherein the dark field photograph of the semiconductor film is taken in a single shot.

22. A method for testing a beam profile comprising:
    irradiating one pulse of an energy beam on a substrate over which an amorphous semiconductor film is formed;
    producing a digital image by taking a visible light dark field photograph of the substrate,
    wherein a direction in which the energy beam has been scanned is a Y direction, and a direction perpendicular to the Y direction is an X direction in the digital image;
    defining a plurality of m×n basic units by dividing the digital image into n columns in the X direction and m rows in the Y direction in a predetermined analysis range in the digital image;
    calculating a sum of corrected saturations of n basic units aligned in the X direction for each of the m rows aligned in the Y direction;
    obtaining an approximate line, one coordinate of a point of the approximate line being a position in the Y direction, and another coordinate of the point being the calculated sum of corrected saturations in the X direction for the position in the Y direction; and
    comparing a fluctuation obtained from relations between the approximate line and the sum of corrected saturations with a reference value which is determined for a demanded performance of a semiconductor element that would comprise the semiconductor film, in order to evaluate a crystallinity of the semiconductor film having crystallinity that has been improved.

23. The method for testing according to claim 22, wherein the visible light used for taking the dark field photograph of the semiconductor film is irradiated from a light source selected from the group consisting of a metal halide lamp, a halogen lamp, a tungsten lamp, a xenon lamp, a light emitting diode, and a fluorescent lamp.

24. The method for testing according to claim 22, wherein an illumination intensity of the visible light used for taking the dark field photograph of the semiconductor film is 10,000 lux or more.

25. The method for testing according to claim 24, wherein the illumination intensity is from 20,000 to 100,000 lux.

26. A manufacturing method of a semiconductor device, comprising:
    testing each of a plurality of semiconductor films crystallized by the energy beam set to different energy densities by the method for testing according to claim 22; and
    determining an irradiation energy density by a result of the testing to crystallize the semiconductor film.

27. The manufacturing method according to claim 26, wherein a means for taking the visible light dark field photograph of the semiconductor film is provided in a crystallization chamber.

28. The method for testing according to claim 22, wherein the visible light used for taking the dark field photograph of the semiconductor film is of an arbitrary wavelength provided it is visible.

29. The method for testing according to claim 22, wherein the visible light used for taking the dark field photograph of the semiconductor film is emitted by a ring light.

30. The method for testing according to claim 22, wherein the dark field photograph of the semiconductor film is taken in a single shot.

31. A method for testing a beam profile comprising:
    irradiating one pulse of an energy beam on a substrate over which an amorphous semiconductor film is formed;
    producing a digital image by taking a visible light dark field photograph of the substrate,
    wherein a direction in which the energy beam has been scanned is a Y direction, and a direction perpendicular to the Y direction is an X direction in the digital image;
    defining a plurality of m×n basic units by dividing the digital image into n columns in the X direction and m rows in the Y direction in a predetermined analysis range in the digital image;
    calculating a sum of luminances of n basic units aligned in the X direction for each of the m rows aligned in the Y direction;
    obtaining an approximate line, one coordinate of a point of the approximate line being a position in the Y direction, and another coordinate of the point being the calculated sum of luminances in the X direction for the position in the Y direction; and
    comparing a fluctuation obtained from relations between the approximate line and the sum of luminances with a reference value which is determined for a demanded performance of a semiconductor element that would comprise the semiconductor film, in order to evaluate a crystallinity of the semiconductor film having crystallinity that has been improved.

32. The method for testing according to claim 31, wherein the visible light used for taking the dark field photograph of the semiconductor film is irradiated from a light source selected from the group consisting of a metal halide lamp, a halogen lamp, a tungsten lamp, a xenon lamp, a light emitting diode, and a fluorescent lamp.

33. The method for testing according to claim 31, wherein an illumination intensity of the visible light used for taking the dark field photograph of the semiconductor film is 10,000 lux or more.

34. The method for testing according to claim 33, wherein the illumination intensity is from 20,000 to 100,000 lux.

35. A manufacturing method of a semiconductor device, comprising:
    testing each of a plurality of semiconductor films crystallized by the energy beam set to different energy densities by the method for testing according to claim 31; and
    determining an irradiation energy density by a result of the testing to crystallize the semiconductor film.

36. The method for testing according to claim 31, wherein the visible light used for taking the dark field photograph of the semiconductor film is of an arbitrary wavelength provided it is visible.

37. The method for testing according to claim 31, wherein the visible light used for taking the dark field photograph of the semiconductor film is emitted by a ring light.

38. The method for testing according to claim 31, wherein the dark field photograph of the semiconductor film is taken in a single shot.

\* \* \* \* \*